United States Patent
Lin et al.

(10) Patent No.: US 7,662,791 B2
(45) Date of Patent: Feb. 16, 2010

(54) GENE SILENCING USING MRNA-CDNA HYBRIDS

(75) Inventors: Shi-Lung Lin, Alhambra, CA (US); Cheng-Ming Chuong, Irvine, CA (US); Randall B. Widelitz, Fullerton, CA (US)

(73) Assignee: University of Southern California, Los Angeles, CA (US)

(*) Notice: Subject to any disclaimer, the term of this patent is extended or adjusted under 35 U.S.C. 154(b) by 0 days.

(21) Appl. No.: 09/920,342

(22) Filed: Aug. 1, 2001

(65) Prior Publication Data

US 2002/0137709 A1    Sep. 26, 2002

Related U.S. Application Data

(60) Provisional application No. 60/222,479, filed on Aug. 2, 2000.

(51) Int. Cl.
A61K 48/00    (2006.01)
(52) U.S. Cl. .................. 514/44; 536/24.31; 536/24.1; 536/24.5
(58) Field of Classification Search .................. 514/44; 536/24.5; 435/6, 91.1
See application file for complete search history.

(56) References Cited

U.S. PATENT DOCUMENTS

| | | | |
|---|---|---|---|
| 4,416,988 A | 11/1983 | Rubin | |
| 4,661,450 A | 4/1987 | Kempe et al. | |
| 4,683,195 A | 7/1987 | Mullis et al. | |
| 4,683,202 A | 7/1987 | Mullis | |
| 4,965,188 A | 10/1990 | Mullis et al. | |
| 5,075,216 A | 12/1991 | Innis et al. | |
| 5,322,770 A | 6/1994 | Gelfand | |
| 6,066,500 A * | 5/2000 | Bennett et al. | 435/375 |
| 6,197,554 B1 | 3/2001 | Lin et al. | |
| 6,506,559 B1 * | 1/2003 | Fire et al. | 435/6 |
| 2004/0087526 A1 | 5/2004 | Lin et al. | |
| 2005/0287668 A1 | 12/2005 | Finney | |

FOREIGN PATENT DOCUMENTS

| | | | |
|---|---|---|---|
| WO | WO 97/24455 | | 7/1997 |
| WO | WO 99/25873 | | 5/1999 |
| WO | WO 02/44321 | * | 2/2002 |

OTHER PUBLICATIONS

Hastie et al. Proc. Natl. Acad. Sci. 1978 75(3)1217-1221.*
Alexeev et al. Nature Biotech. 2000, 18:43-47.*
Parrish et al. Functional Anatomy of a dsRNA trigger: differential requirements for the two trigger strands in RNA interference. Molecular Cell, 2000, vol. 6: 1077-1087. Cell Press.*
Caplen NJ. RNAi as a Gene Therapy Approach. Expert Opinon. Biol. Thera. (2003) vol. 3(4) 575-586. Ashley Publications Ltd.*
Paroo et al. Challenges for RNAi in vivo. Trends in Biotechnology (2004), vol. 22(8) 390-394. Elsevier.*
Novina et al. The RNAi Revolution. Nature 2004, vol. 430: 161-164. Nature Publishing Group.*
Chamberlin, M., et al., "New RNA Polymerease from *Escherichia coli* Infected with Bacteriophage T7," *Nature* 228, 227-231 (1970).
Cogoni, C., et al., "Gene Silencing in *Neurospora crassa* Requires a Protein Homologous to RNA-Dependent RNA Polymerase," *Nature*, 399, 166-169 (1999).
Compton, J., "Nucleic Acid Sequence-Based Amplification," *Nature*, 350, 91-92 (1991).
Fire, A., et al., "Potent and Specific Genetic Interference by Double-Stranded RNA in *Caenorhabditis elegans*," *Nature*, 391, 806-811 (1998).
Wianny, F., et al., "Specific Interference with Gene Function by Double-Stranded RNA in Early Mouse Development," *Nature Cell Biology*, 2, 70-75 (2000).
Embleton, M.J., et al., "In-Cell PCR from mRNA: Amplifying and Linking the Rearranged Immunoglobulin Heavy and Light Chain V-Genes within Single Cells," *Nucleic Acids Research*, 20(15), 3831-3837 (1992).
Lin, S.-L., et al., "In Vivo Analysis of Cancerous Gene Expression by RNA-Polymerase Chain Reaction," *Nucleic Acids Research*, 27(23) 4585-4589 (1999).
Eberwine, J., et al., "Analysis of Gene Expression in Single Live Neurons," *Proc. Natl. Acad. Sci. USA*, 89, 3010-3014 (1992).
Kacian, D.L., et al., "A Replicating RNA Molecule Suitable for a Detailed Analysis of Extracellular Evolution and Replication," *Proc. Nat. Acad. Sci. USA*, 69(10), 3038-3042 (1972).
Misquitta, L., et al., "Targeted Disruption of Gene Function in *Drosophila* by RNA Interference (RNA-i): A Role for Nautilus in Embryonic Somatic Muscle Formation," *Proc. Natl. Acad. Sci. USA*, 96, 1451-1456 (1999).
Filipovska, J., et al., "Specific HDV RNA-Templated Transcription by Pol II In Vitro," *RNA*, 6, 41-54, (2000).
Grishok, A., et al., "Genetic Requirements for Inheritance of RNAi in *C. elegans*," *Science*, 287, 2494-2497 (2000).
Shimoda-Matsubayashi, et al., "Structural Dimorphism in the Mitochondrial Targeting Sequence in the Human Manganese Superoxide Dismutase Gene: A Predictive Evidence for Conformational Change to Influence Mitochondrial Transport and a Study of Allelic Association in Parkinson's Disease," *Biochemical and Biophysical Research Communications*, 226, 561-565, Art. No. 1394, (1996).

(Continued)

*Primary Examiner*—Kimberly Chong
(74) *Attorney, Agent, or Firm*—Hogan & Hartson LLP

(57) ABSTRACT

The present invention provides novel compositions and methods for suppressing the expression of a targeted gene using mRNA-cDNA duplexes. The invention further provides novel methods and compositions for generating amplified mRNA-cDNA hybrids, whose quantity is high enough to be used for the invention's gene silencing transfection. This improved RNA-polymerase chain reaction method uses thermocycling steps of promoter-linked double-stranded cDNA or RNA synthesis, in vitro transcription and then reverse transcription to amplify the amount of mRNA-cDNA hybrids up to two thousand folds within one round of the above procedure.

7 Claims, 10 Drawing Sheets

OTHER PUBLICATIONS

Ambrosone, C.B., et al., "Manganese Superoxide Dismutase (MnSOD) Genetic Polymorphisms, Dietary Antioxidants, and Risk of Breast Cancer," *Cancer Research*, 59, 602-606, (1999).

Lin, S.-L., et al., "Differentially Expressed Genes in Activin-Induced Apoptotic LNCaP Cells," *Biochemical and Biophysical Research Communications*, 257, 187-192 (1999).

Wargelius, A., et al., "Double Stranded RNA Induces Specific Developmental Defects in Zebrafish Embryos," *Biochemical and Biophysical Research Communications*, 263, 156-161 (1999).

Myers, et al., "Reverse Transcription and DNA Amplification by a *Thermus thermophilus* DNA Polymerase," *Biochemistry*, 30:31, 7661-7666 (1991).

Grant, S. R., "Dissecting the Mechanisms of Posttranscriptional Gene Silencing: Divide and Conquer," *Cell*, 96, 303-306 (1999).

Kennerdell, J.R., et al., "Use of dsRNA-Mediated Genetic Interference to Demonstrate that frizzled and frizzled 2 Act in the Wingless Pathway," *Cell*, 95, 1017-1026 (1998).

Ketting, R.F., et al., "mut-7 of *C. elegans*, Required for Transposon Silencing and RNA Interference, is a Homolog of Werner Syndrome Helicase and RNaseD," *Cell*, 99, 133-141 (1999).

Pal-Bhadra, M., et al., "Cosuppression of Nonhomologous Transgenes in *Drosophila* Involves Mutually Related Endogenous Sequences," *Cell*, 99, 35-46 (1999).

Tabara, H., et al., "The rde-1 Gene, RNA Interference, and Transposon Silencing in *C. elegans*," *Cell*, 99, 123-132 (1999).

Zamore, P.D., et al., "RNAi: Double-Stranded RNA Directs the ATP-Dependent Cleavage of mRNA at 21 to 23 Nucleotide Intervals," *Cell*, 101, 25-33 (2000).

Smardon, A., et al., "EGO-1 is Related to RNA-Directed RNA Polymerase and Functions in Germ-Line Development and RNA Interference in *C. elegans*," *Current Biology*, 10, 169-178 (2000).

Yang, D., et al., "Evidence that Processed Small dsRNAs May Mediate Sequence-Specific mRNA Degradation During RNAi in *Drosophila* Embryos," *Current Biology*, 10, 1191-1200 (2000).

Modahl, L.E., et al., "RNA-Dependent Replication and Transcription of Hepatitis Delta Virus RNA Involve Distinct Cellular RNA Polymerases," *Molecular and Cellular Biology*, 20(16), 6030-6039 (2000).

Sambrook et al., "Molecular Cloning: Northern Hybridization," $2^{nd}$ Ed., *Cold Spring Harbor Laboratory Press*, 7.39-7.52 (1989).

Lin, Shi-Lung et al. "A Novel mRNA-cDNA Interference Phenomenon for Silencing bcl-2 Expression Human LNCaP Cells" Biochemical and Biophysical Research Communications 281, 639-644 (2001).

Bosher, Julia M. et al. "RNA Interference: Genetic Wand and Genetic Watchdog" Nature Cell Biology, vol. Feb. 2000.

Lin et al., "D-RNAi (Messenger RNA-antisense DNA Interference) as a Novel Defense System Against Cancer and Viral Infections," Current Cancer Drug Targets, 2001, pp. 241-247.

Lin et al., "Novel RNAi Therapy—Intron-Derived MicroRNA Drugs," Drug Design Reviews—Online, 2004, I, pp. 1-9.

Lin et al., "A Novel mRNA-cDNA Interference Phenomenon for Silencing bcl-2 Expression in Human LNCaP Cells," Biochemical and Biophysical Research Communications 281, 2001, pp. 639-644.

International Search Report for corresponding PCT application PCT/US08/79638 lists the references above.

* cited by examiner

GENE SILENCING USING MRNA-CDNA HYBRIDS

RELATED APPLICATION DATA

This applications claims priority to U.S. provisional application Ser. No. 60/222,479, filed Aug. 2, 2000, the entire disclosure of which is incorporated herein by this reference.

STATEMENT REGARDING FEDERALLY SPONSORED RESEARCH OR DEVELOPMENT

This invention was made with government support under Contract No. CA083716 awarded by the National Institutes of Health. The government has certain rights in the invention.

FIELD OF THE INVENTION

The present invention relates generally to gene silencing phenomenon, and particularly to gene silencing using mRNA-cDNA hybrids and methods for generating mRNA-cDNA hybrids for use in gene silencing.

BACKGROUND OF THE INVENTION

Gene silencing or inhibiting the expression of a gene holds great therapeutic and diagnostic promise. An example of this approach is antisense technology which can be used to inhibit gene expression in vivo. However, many problems remain with development of effective antisense technology. For example, DNA antisense oligonucleotides exhibit only short term effectiveness and are usually toxic at the doses required. Similarly, the use of antisense RNAs has also proved ineffective due to stability problems.

Other approaches to quelling specific gene activities are posttranscriptional gene silencing (PTGS) and RNA interference (RNAi) phenomena, which have been found capable of suppressing gene activities in a variety of in-vivo systems, including plants (Grant, S. R. (1999) *Cell* 96, 303-306), *Drosophila melanogaster* (Kennerdell, J. R. and Carthew, R. M. (1998) Cell 95, 1017-1026, Misquitta, L. and Paterson, B. M. (1999) *Proc. Natl. Acad. Sci. USA* 96, 1451-1456, and Pal-Bhadra, M., Bhadra, U., and Birchler, J. A. (1999) *Cell* 99, 35-46), *Caenorhabditis elegans* (Tabara, H., Sarkissian, M., Kelly, W. G., Fleenor, J., Grishok, A., and Timmons, L. (1999) *Cell* 99, 123-132, Ketting, R. F., Haverkamp, T. H., van Luenen, H. G., and Plasterk, R. H. (1999) *Cell* 99, 133-141, Fire, A., Xu, S., Montgomery, M. K., Kostas, S. A., Driver, S. E., and Mello, C. C. (1998) *Nature* 391, 806-811 and Grishok, A., Tabara, H., and Mello, C. C. (2000) *Science* 287, 2494-2497), zebrafish (Wargelius, A., Ellingsen, S., and Fjose, A. (1999) *Biochem. Biophys. Res. Commun.* 263, 156-161) and mouse (Wianny, F. and Zernicka-Goetz, M. (2000) *Nature Cell Biol.* 2, 70-75). In general, the transfection of a plasmid-like DNA structure (transgene) into cells induces PTGS phenomena, while that of a double-stranded RNA (dsRNA) causes an RNAi effect.

These phenomena appear to evoke an intracellular sequence-specific RNA degradation process, affecting all highly homologous transcripts, called cosuppression. It has been proposed that such cosuppression results from the generation of small RNA products (21~25 nucleotide bases) by an RNA-directed RNA polymerase (RdRp) (Grant supra) and/or a ribonuclease (RNase) (Ketting et al. supra, Bosher, J. M. and Labouesse, M. (2000) *Nature Cell Biology* 2, 31-36 and Zamore, P. D., Tuschl, T., Sharp, P. A., and Bartel, D. P. (2000) *Cell* 101, 25-33.) activity on an aberrant RNA template, derived from the transfecting nucleic acids or viral infection. Although an RdRp-independent endoribonucleolysis model has been proposed for the RNAi effect in *Drosophila* (Zamore, et al. supra), the RdRp homologues were widely found in *Arabidopsis thalianas* as Sde-1/Sgs-2 (Yang, D., Lu, H., and Erickson, J. W. (2000) *Current Biology* 10, 1191-1200), *Neurospora crassa* as Qde-1 (Cogoni, C. and Macino, G. (1999) *Nature* 399, 166-169) and *Caenorhabditis elegans* as Ego-1 (Smardon, A., Spoerke, J. M., Stacey, S. C., Klein, M. E., Mackin, N., and Maine, E. M. (2000) *Curr. Biol.* 10, 169-171). Thus, RdRp homologues appear to be a prerequisite for maintaining a long-term/inheritable PTGS/RNAi effect (Bosher, et al. supra).

Although PTGS/RNAi phenomena appear to offer a potential avenue for inhibiting gene expression, they have not been demonstrated to work well in higher vertebrates and, therefore, their widespread use in higher vertebrates is still questionable. Consequently, there remains a need for an effective and sustained method and composition for inhibiting gene function in vivo in higher vertebrates.

SUMMARY OF THE INVENTION

The present invention provides a novel composition and method for inhibiting gene function in prokaryotes and eukaryotes in vivo and in vitro. Without being bound by any particular theory, this method potentially is based on an RdRp-dependent gene silencing phenomenon, similar to PTGS/RNAi, which is hereafter termed DNA-RNA interference (D-RNAi). In accordance with the present invention, mRNA-cDNA hybrids are used for inhibiting gene function. The mRNA-cDNA hybrids of the present invention can be used to target a gene selected from the group consisting of pathogenic nucleic acids, viral genes, mutated genes, and oncogenes.

In specific embodiments, the present invention provides a composition for inhibiting the expression of a targeted gene in a substrate wherein the composition comprises an mRNA-cDNA hybrid. The composition of the invention is effective to inhibit the expression of the targeted gene in vitro or in vivo. The mRNA-cDNA hybrid may be synthesized using the method described below. In one embodiment, the mRNA of the invention's hybrids is comprised of part or all of the unspliced mRNA transcript of the targeted gene. In another embodiment, the mRNA is comprised of part or all of the spliced mRNA transcript of the targeted gene. In yet another embodiment, the mRNA is comprised of a combination of part or all of the spliced and unspliced mRNA transcript of the targeted gene. To prepare the composition, the mRNA-cDNA hybrid may be prepared by complementarily combining the sense-oriented mRNA of one of the three preceding embodiments with its corresponding antisense-oriented cDNA molecule in a base-pairing double stranded form.

The composition of the invention may be used to treat a substrate that is a cell or an organism, which may be either prokaryotic or eukaryotic.

The composition of the invention may be administered to the substrate using methods and compositions known to one of ordinary skill in the art. For example, the composition of the invention may further comprise a carrier molecule, which is capable of being taken up by a cell. The compositions may be administered orally, intravenously, transdermally, etc.

Further, the present invention provides a method for inhibiting the expression of a targeted gene in a substrate, comprising the steps of: a) providing a composition comprising an mRNA-cDNA hybrid capable of inhibiting the expression of the targeted gene in the substrate and b) contacting the substrate with the composition under conditions such that gene expression in the substrate is inhibited. The substrate can express the targeted gene in vitro or in vivo. The composition to be used in this method of the invention may be a composition selected from one of the above-described compositions.

In one embodiment, the mRNA-cDNA hybrid targets a gene selected from the group consisting of pathogenic nucleic acids, viral genes, mutated genes, and oncogenes. In another embodiment, the mRNA-cDNA hybrid inhibits β-catenin expression. In yet another embodiment, the mRNA-cDNA hybrid inhibits bcl-2 expression. In various embodiments, the substrate is a prokaryote, e.g., a virus or a bacterial cell, or a eukaryote or the cell of a eukaryote. Eukaryotes contemplated by the invention include, without limitation, vertebrates, e.g., mice, chimpanzees and humans.

The invention also provides compositions and methods for preparing mRNA-cDNA hybrids. Specifically, the present invention provides methods for generating mRNA-cDNA hybrids, comprising the steps of: a) providing: i) a solution comprising a nucleic acid template, ii) one or more primers sufficiently complementary to the sense conformation of the nucleic acid template, and iii) one or more promoter-linked primers sufficiently complementary to the antisense conformation of the nucleic acid template, and having an RNA promoter; b) treating the nucleic acid template with one or more primers under conditions such that a first cDNA strand is synthesized; c) treating the first cDNA strand with one or more promoter-linked primers under conditions such that a promoter-linked double-stranded nucleic acid is synthesized; d) treating the promoter-linked double-stranded nucleic acid under conditions such that essentially mRNA fragments are synthesized; and e) treating mRNA fragments with one or more primers under conditions such that an mRNA-cDNA hybrid is synthesized. The methods of the present invention can comprise the step of repeating steps b) through e) for a sufficient number of cycles to obtain a desired amount of amplified product.

The treating step in step b) can comprise heating the solution at a temperature above 90° C. to provide denatured nucleic acids. The treating step in step c) can comprise treating the first cDNA strand with one or more promoter-linked primers at a temperature ranging from about 35° C. to about 75° C. The treating step in step c) can also comprise treating the EDNA strand with one or more promoter-linked primers in the presence of a polymerase.

In one embodiment, the polymerase is selected from the group consisting of DNA-dependent DNA polymerases, RNA-dependent DNA polymerases, RNA polymerases, Taq-like DNA polymerase, TTh-like DNA polymerase, C. therm. polymerase, viral replicases, and combinations thereof. The viral replicases can be selected from the group consisting of avian myeloblastosis reverse transcriptase and Moloney murine leukemia virus reverse transcriptase. In particular, the AMV reverse transcriptase does not have RNase activity.

The treating step in step d) can comprise treating the promoter-linked double-stranded nucleic acid with an enzyme having transcriptase activity at about 37° C. The enzyme having transcriptase activity can be selected from the group consisting of RNA polymerases and viral replicases. The RNA polymerases can be selected from the group consisting of T3 RNA polymerase, T7 RNA polymerase, SP6 RNA polymerase, and M13 RNA polymerase.

The primers are complementary to the 3'-ends of the sense conformation of the nucleic acid template. In one embodiment, one or more primers comprise a poly(dT)$_{24}$ primer.

The promoter-linked primers are complementary to the 5'-ends of the antisense conformation of the nucleic acid template. In one embodiment, one or more promoter-linked primers comprise oligo(dC)$_{10}$N-promoter primers. The oligo (dC)$_{10}$N-promoter primers can also comprise oligo(dC)$_{10}$G-T7 primers, oligo(dC)$_{10}$A-T7 primers, oligo(dC)$_{10}$T-T7 primers, and combinations thereof. The promoter-linked double-stranded nucleic acid can be selected from the group consisting of promoter-linked double-stranded DNAs and promoter-linked double-stranded RNAs.

In one embodiment, the treating step in step e) comprises treating mRNA fragments with one or more primers at a temperature ranging from about 35° C. to about 75° C.

The methods of the present invention can further comprise the step of incorporating one or more nucleotide analogs into the cDNA portion of the mRNA-cDNA hybrid to prevent degradation. In another embodiment, the methods of the present invention further comprise the step of contacting mRNA-cDNA hybrids with a reagent for gene knockout transfection. The reagent can be selected from the group consisting of chemical transfection reagents and liposomal transfection reagents.

The present invention relating to mRNA-cDNA gene knockout technology can be used as a powerful new strategy in the field of antisense gene therapy. The strength of this novel strategy is in its low dose, stability, and potential long-term effects. Applications of the present invention include, without limitation, the suppression of cancer related genes, the prevention and treatment of microbe related genes, the study of candidate molecular pathways with systematic knock out of involved molecules, and the high throughput screening of gene functions based on microarray analysis, etc. The present invention can also be used as a tool for studying gene function in physiological conditions.

BRIEF DESCRIPTION OF THE DRAWINGS

FIG. 9A shows the embryo prior to microinjection; FIG. 9B shows the embryo after injection. FIG. 9C shows the Northern analyses results after treatment with mRNA-cDNA hybrid, while FIG. 9D shows the liposome control embryos.

DEFINITIONS

Figure 1:
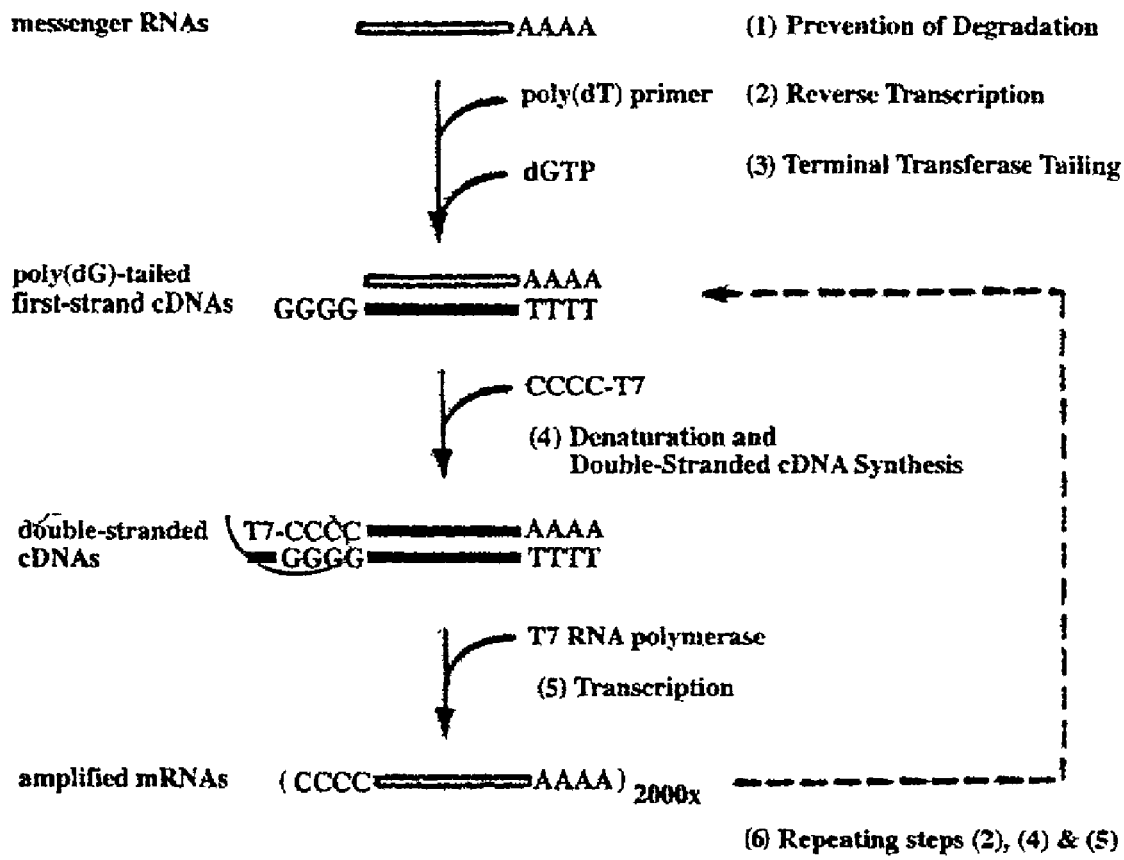
FIG. 1 shows a schematic representation of the RNA-PCR method for RNA amplification.

To facilitate understanding of the invention, a number of terms are defined below.

As used herein, the terms "complementary" or "complementarity" are used in reference to polynucleotides (i.e., a sequence of nucleotides) related by the base-pairing rules. For example, the sequence "A-G-T" is complementary to the sequence "T-C-A." Complementarity may be "partial," in which only some of the nucleic acid bases are matched according to the base pairing rules. Alternatively, complementarity may be "complete" or "total" between the nucleic acids. The degree of complementarity between nucleic acid strands has significant effects on the efficiency and strength of hybridization between nucleic acid strands. This is of particular importance in amplification reactions, as well as in detection methods which depend upon binding between nucleic acids.

As used herein, the term "template" refers to a nucleic acid molecule being copied by a nucleic acid polymerase. A template can be single-stranded, double-stranded or partially double-stranded, depending on the polymerase. The synthesized copy is complementary to the template, or to at least one strand of a double-stranded or partially double-stranded template. Both RNA and DNA are synthesized in the 5' to 3' direction. The two strands of a nucleic acid duplex are always aligned so that the 5' ends of the two strands are at opposite ends of the duplex (and, by necessity, so then are the 3' ends).

As used herein, the term "mRNA" or "messenger RNA" refers to a single stranded RNA molecule that is synthesized during transcription, is complementary to one of the strands of double-stranded DNA, and serves to transmit the genetic information contained in DNA to the ribosomes for protein synthesis. The mRNA may be spliced, partially spliced or unspliced, and may be eukaryotic or prokaryotic mRNA.

As used herein, the term "nucleic acid template" refers to a double-stranded DNA/RNA, a single-stranded DNA, an mRNA/aRNA or an RNA-DNA hybrid.

As used herein, the term "poly (dT)n promoter sequence" refers to an RNA polymerase promoter sequence coupled with a poly-deoxythymidylate (dT) sequence at its 3' end, in which the number n of linked dTs lies in the range of about five to about thirty and most preferably about twenty six.

As used herein, the term "oligo(dC)nN-T7 primer" refers to an RNA primer coupled with a poly-deoxycytidylate (dC). The number n of total incorporated nucleotides is in the range of about 5 to about 30 and is most preferably about 12.

As used herein, the term "primer" refers to an oligonucleotide complementary to a template. The primer complexes with the template to give a primer/template complex for initiation of synthesis by a DNA polymerase. The primer/template complex is extended by the addition of covalently bonded bases linked at its 3' end, which are complementary to the template in DNA synthesis. The result is a primer extension product. Virtually all known DNA polymerases (including reverse transcriptases) require complexing of an oligonucleotide to a single-stranded template ("priming") to initiate DNA synthesis.

As used herein, the term "promoter-linked primer" refers to an RNA-polymerase-promoter sense sequence coupled with a gene-specific complementary sequence in its 3'-end for annealing to the antisense conformation of a nucleic acid template.

As used herein, the term "DNA-dependent DNA polymerase" refers to an enzyme that synthesizes a complementary DNA copy from a DNA template. Examples are DNA polymerase I from $E.\ coli$ and bacteriophage T7 DNA polymerase. Under suitable conditions a DNA-dependent DNA polymerase may synthesize a complementary DNA copy from an RNA template.

As used herein, the terms "DNA-dependent RNA polymerase" and "transcriptase" refer to enzymes that synthesize multiple RNA copies from a double-stranded or partially-double stranded DNA molecule having a promoter sequence. Examples of transcriptases include, but are not limited to, DNA-dependent RNA polymerase from $E.\ coli$ and bacteriophages T7, T3, and SP6.

As used herein, the terms "RNA-dependent DNA polymerase" and "reverse transcriptase" refer to enzymes that synthesize a complementary DNA copy from an RNA template. All known reverse transcriptases also have the ability to make a complementary DNA copy from a DNA template. Thus, reverse transcriptases are both RNA-dependent and DNA-dependent DNA polymerases. As used herein, the term "RNAse H" refers to an enzyme that degrades the RNA portion of an RNA/DNA duplex. RNAse H's may be endonucleases or exonucleases. Most reverse transcriptase enzymes normally contain an RNAse H activity in addition to their polymerase activity. However, other sources of the RNAse H are available without an associated polymerase activity. The degradation may result in separation of RNA from a RNA/DNA complex. Alternatively, the RNAse H may simply cut the RNA at various locations such that portions of the RNA melt off or permit enzymes to unwind portions of the RNA.

As used herein, the terms "hybridize" and "hybridization" refer to the formation of complexes between nucleotide sequences which are sufficiently complementary to form complexes via Watson-Crick base pairing. Where a primer (or splice template) "hybridizes" with target (template), such complexes (or hybrids) are sufficiently stable to serve the priming function required by the DNA polymerase to initiate DNA synthesis.

As used herein, the term "sense conformation" refers to a nucleic acid sequence in the same sequence order and composition as its homolog mRNA.

As used herein, the term "antisense conformation" refers to a nucleic acid sequence complementary to its respective mRNA homologue. The antisense RNA (aRNA) refers to a ribonucleotide sequence complementary to an mRNA sequence in an A-U and C-G composition, and also in the reverse orientation of the mRNA.

As used herein, the term "gene" refers to a nucleic acid (e.g., DNA) sequence that comprises coding sequences necessary for the production of a polypeptide or precursor. The polypeptide can be encoded by a full length coding sequence or by any portion of the coding sequence so long as the desired activity or functional properties (e.g., enzymatic activity, ligand binding, signal transduction, etc.) of the full-length or fragment are retained. The term "gene" encompasses both cDNA and genomic forms of a gene. A genomic form or clone of a gene contains the coding region interrupted with non-coding sequences termed "intervening regions" or "intervening sequences."

As used herein, the term "gene silencing" refers to a phenomenon whereby a function of a gene is completely or partially inhibited. Throughout the specification, the terms "silencing," "inhibition," "quelling," "knockout" and "suppression," when used with reference to gene expression or function, are used interchangeably.

As used herein, the term "oligonucleotide" is defined as a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

As used herein, the term "transfection" refers to the introduction of foreign DNA into eukaryotic cells. Transfection can be accomplished by a variety of means known to the art, including, but not limited to, calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

A primer is selected to be "substantially" or "sufficiently" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

As used herein, the term "amplification" refers to nucleic acid replication involving template specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that will process only specific sequences of nucleic acid in a heterogeneous mixture of nucleic acid. For example, in the case of Qβ replicase, MDV-1 RNA is the specific template for the replicase (Kacian et al., *Proc. Natl. Acad. Sci. USA* 69:3038 (1972)). Other nucleic acid will not be replicated by this amplification enzyme. Similarly, in the case of T7 RNA polymerase, this amplification enzyme has a stringent specificity for its own promoters (Chamberlin et al., *Nature* 228:227 (1970)). Taq and Pfu polymerases, by virtue of their ability to function at high temperature display high specificity for the sequences bounded, and thus defined by the primers.

As used herein, the terms "amplifiable nucleic acid" and "amplified products" refer to nucleic acids which may be amplified by any amplification method.

As used herein, the term "probe" refers to an oligonucleotide (i.e., a sequence of nucleotides) which is capable of hybridizing to another oligonucleotide of interest, whether occurring naturally as in a purified restriction digest or produced synthetically, recombinantly or by PCR amplification. A probe may be single-stranded or double-stranded. Probes are useful in the detection, identification and isolation of particular gene sequences.

As used herein, the term "polymerase chain reaction" ("PCR") refers to a method for increasing the concentration of a segment in a target sequence from a mixture of genomic DNA without cloning or purification (U.S. Pat. Nos. 4,683, 195; 4,683,202; and 4,965,188, hereby incorporated by reference). This process for amplifying the target sequence consists of introducing a large excess of two oligonucleotide primers to the DNA mixture containing the desired target it sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" ("PCR"). Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g., incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

As used herein, the term "portion" when in reference to a protein or nucleic acid sequence refers to fragments of that protein or nucleic acid sequence. Fragments of a protein can range in size from four amino acid residues to the entire amino acid sequence minus one amino acid.

The term "nucleotide analog" as used herein refers to modified or non-naturally occurring nucleotides such as 7-deaza purines (i.e., 7-deaza-dATP and 7-deaza-dGTP). Nucleotide analogs include base analogs and comprise modified forms of deoxyribonucleotides as well as ribonucleotides.

The term "Northern blot," as used herein refers to the analysis of RNA by electrophoresis of RNA on agarose gels to fractionate the RNA according to size, followed by transfer of the RNA from the gel to a solid support such as nitrocellulose or a nylon membrane. The immobilized RNA is then probed with a labeled probe to detect RNA species complementary to the probe used. Northern blots are a standard tool of molecular biologists (Sambrook et al., *Molecular Cloning*, 2$^{nd}$ Ed., Cold Spring Harbor Laboratory Press, pp 7.39-7.52 (1989)).

As used herein, the term "Southern blot" refers to the analysis of DNA on agarose or acrylamide gels to fractionate the DNA according to size, followed by transfer of the DNA from the gel to a solid support such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (Sambrook et al., supra).

The term "virus" refers to obligate, ultramicroscopic, intracellular parasites incapable of autonomous replication (i.e., replication requires the use of the host cell's machinery).

As used herein, the terms "Taq-like polymerase" and "Taq polymerase" refer to Taq DNA polymerase and derivatives. Taq DNA is widely used in molecular biology techniques including recombinant DNA methods. For example, various forms of Taq have been used in a combination method which utilizes PCR and reverse transcription (See e.g., U.S. Pat. No. 5,322,770, incorporated herein in its entirety by reference). DNA sequencing methods which utilize Taq DNA polymerase have also been described. (See e.g., U.S. Pat. No. 5,075,216, incorporated herein in its entirety by reference).

As used herein, the terms "TTh-like polymerase" and "TTh polymerase" refer to polymerase isolated from *Thermus thermophilus*. Tth polymerase is a thermostable polymerase that can function as both reverse transcriptase and DNA polymerase (Myers and Gelfand, *Biochemistry* 30:7662-7666 (1991)). It is not intended that the methods of the present invention be limited to the use of Taq-like or TTh-like polymerases. Other thermostable DNA polymerases which have 5' to 3' exonuclease activity (e.g., Tma, Tsps17, TZ05, Tth and Taf) can also be used to practice the compositions and methods of the present invention.

DETAILED DESCRIPTION OF THE INVENTION

The present invention relates to compositions and methods for generating mRNA-cDNA hybrids and compositions and methods using the same for gene silencing. It is proposed that the mRNA-cDNA hybrids effect an RdRp-dependent gene silencing phenomenon, i.e., DNA-RNA interference (D-RNAi). The advantages of using D-RNAi instead of ds-RNA are as follows: 1) the cDNA part of a D-RNAi can be modified by nucleotide-analog incorporation to increase the stability and effectiveness of transfected probe activities; 2) the RdRp enzyme may provide higher affinity to the mRNA template of a D-RNAi compared to a ds-RNA due to lower binding interaction between DNA-RNA duplexes than RNA-RNA duplexes; and 3) the cDNA part of a D-RNAi provides further antisense gene knockout activity in addition to the PTGS gene silencing mechanisms of the sense-RNA template, resulting in multiple specific gene interference effects with one probe.

The m-RNA-cDNA hybrids of the invention are preferably prepared using an improvement of the so-called RNA-PCR described in U.S. Pat. No. 6,197,554.

RNA-PCR

A PCR-like reaction performed on mRNAs, named the RNA-polymerase chain reaction (RNA-PCR), to provide a highly efficient amplification (~250-fold/cycle) of the whole mRNA repertoire exists in the prior art. (Lin et al., *Nucl. Acids. Res.* 27:4585-4589 (1999)); U.S. Pat. No. 6,197,554 to Lin et al., incorporated herein by reference in their entirety). The elevated thermocycling temperature prevents rapid degradation of short-lived mRNAs and further reduces the secondary structure of mRNAs to increase the accessibility of enzyme interactions and the production of more complete full-length mRNAs. The procedure uses thermostable enzymes, including Tth-like DNA polymerases with reverse transcriptase activity and thermostable RNA polymerases. The use of proofreading RNA polymerases for amplification not only provides higher fidelity but also eliminates preferential amplification of abundant mRNA species. Additionally, rapid and simple cell fixation and permeabilization steps inhibit any alterations in gene expression during specimen handling or genomic contamination. (See, Embleton et al., *Nucl. Acids Res.* 20: 3831-3837 (1992)).

The procedure, depicted in FIG. 1, is as follows: (1) prevention of mRNA degradation; (2) first reverse transcription; (3) a tailing reaction to add 5'-poly(dT) and 3'-poly(dG) to the first strand cDNAs; (4) denaturation and then cDNA double-stranding by the extension of an oligo(dC)-promoter primer complementary to the 3'-poly(dG) tail; (5) promoter-driven transcription to amplify mRNAs up to 2000-fold in one cycle; (6) repeating steps 2, 4 and 5 (without 3) to achieve the desired mRNA amplification.

The procedure can be implemented using a poly(dT)$_{24}$ primer to generate the first-strand cDNAs. Another oligo (dC)-promoter primer is used to generate the second-strand cDNAs. Both strands together form the promoter-linked double-stranded cDNAs from the original mRNAs. The oligo (dC)-promoter primer is an equal mixture of oligo(dC)$_{10}$N sequences (N=dG, dA or dT) coupled to an RNA promoter for in vitro transcription along the doublestranded cDNA templates. Because the promoter region is incorporated in the 5'-end of the second-strand cDNAs which has the same sequence and composition as the original mRNAs, the transcription products are all in the form of mRNAs, not aRNAs. These amplified mRNAs not only share the same properties but also have the full integrity of their original mRNAs, depending on the quality of the first promoter-linked double-stranded cDNAs.

Methods for Generating mRNA-cDNA Hybrids for Gene Silencing

The present invention provides a simple, fast, and inexpensive method for amplifying specific mRNA-cDNA hybrids for gene silencing transfection. The mRNA-cDNA hybrids can be used for screening special gene functions, for manipulating gene expressions in vitro, and for designing a therapy for genetic diseases in vivo.

Figure 7:
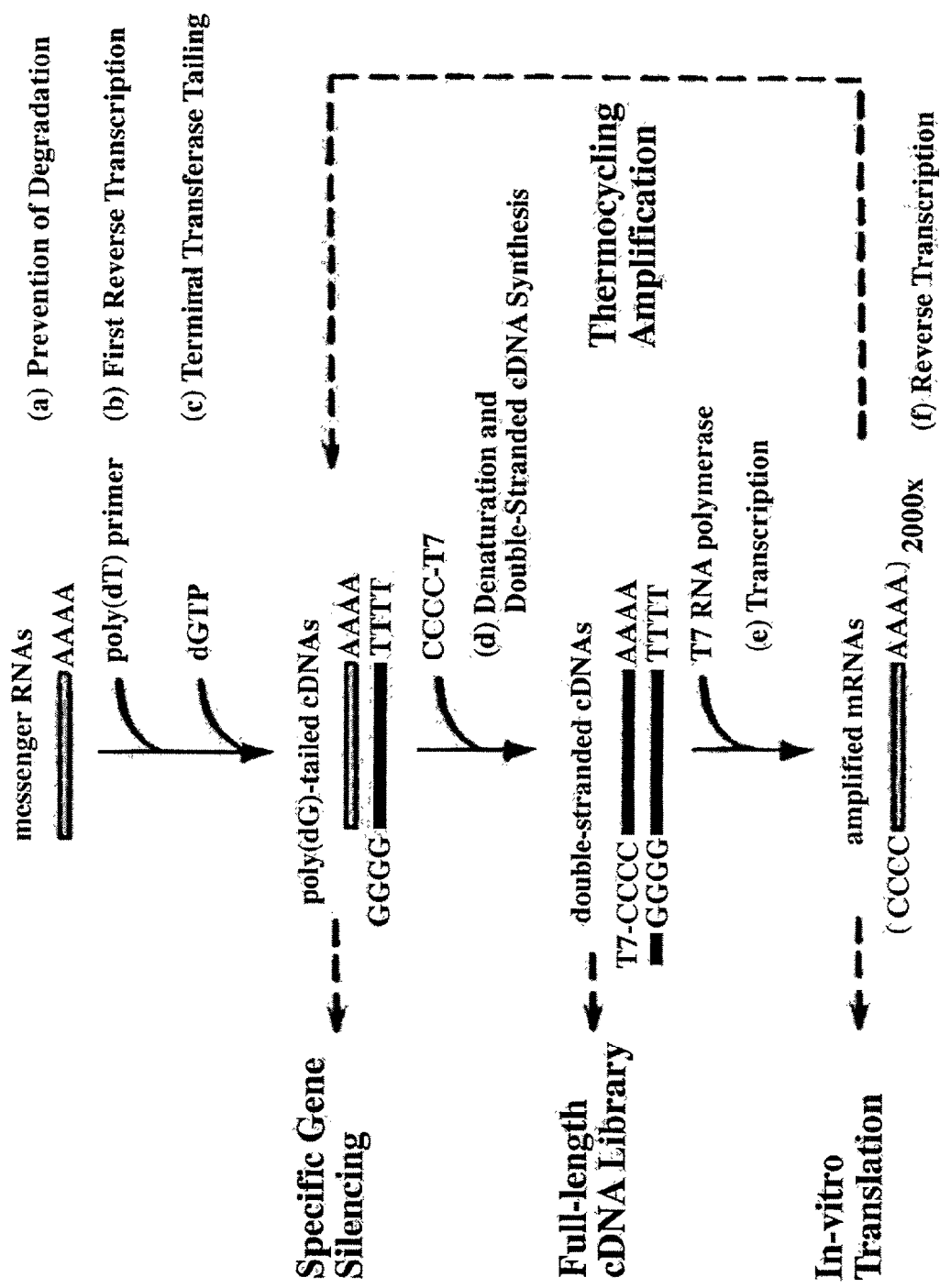
FIG. 7 shows a schematic representation for producing mRNA-cDNA hybrids.

The present invention is directed to an improved RNA-polymerase chain reaction method for generating mRNA-cDNA hybrid duplexes (FIG. 7) for gene interference effects in cells ("D-RNAi").

An improved RNA-PCR method that uses a gene-specific primer and promoter-primer in a thermocycling procedure to amplify specific mRNA-cDNA sequences is provided. This thermocycling procedure preferably starts from reverse transcription of mRNAs with Tth-like polymerases, following a promoter-incorporation and cDNA double-stranding reaction with the same Tth-like polymerases. The resulting promoter-linked double-stranded DNAs serve as transcriptional templates for amplifying mRNA up to 2000 fold/cycle by RNA polymerases. Alternatively, RNA replicases can be used to directly amplify mRNA when the starting templates are aRNAs or ds-RNAs containing a functional recognition site for the replicases. The thermocycling procedure can be repeated for more amplification to a desired amount of mRNA-cDNA hybrids.

The amplification cycling procedure of the present invention presents several advantages over prior amplification methods. First, D-RNAi probes from low-copy rare mRNA species can be prepared within three rounds of amplification cycling without misreading mistakes. Second, the mRNA-cDNA hybrid amplification is linear and does not result in preferential amplification of nonspecific gene sequences. Third, mRNA degradation is inhibited by thermostable enzymatic conditions without RNase activities. Finally, the use of RNase H activity is restricted, thereby preserving the integrity of final mRNA-cDNA constructs. Unlike current NASBA methods (Compton, *Nature* 350: 91-92 (1991)), this improved RNA-PCR procedure contains no RNase H activity which can degrade the RNA structure of a RNA-DNA hybrid. Thus, the methods of the present invention can be used to prepare high amounts of pure and specific mRNA-cDNA hybrids for transducing biological effects of interest in vitro as well as in vivo.

The labeling of mRNA-cDNA hybrids can be accomplished by incorporation of labeled nucleotides or analogs during reverse transcription of Tth-like polymerase activity. The mRNA-cDNA hybrids of the present invention can be used as probes in a variety of applications, including but not limited to, Northern blots, Southern blots, dot hybridization, in situ hybridization, position cloning, nucleotide sequence detection, and antisense knockout transfection. The mRNA-cDNA structures can also comprise nucleotide analogs to prevent degradation, resulting in more stability and effectiveness of the probe transfection. In addition to the gene silencing effects (or PTGS) caused by the mRNA part, the antisense cDNA part of the mRNA-cDNA hybrids can further provide traditional gene knockout schemes through the binding of itself to intracellular mRNA homologues. Both gene knockout effects ensure the success of degrading certain specific mRNA species in cells, causing a broad and multiple gene interference result better than previous antisense gene knockout methodology.

Although certain preferred embodiments of the present invention have been described, the spirit and scope of the invention is by no means restricted to what is described above. For example, different nucleic acid templates, as well as different specific primers for reverse transcription and polymerase extension reaction can be used to practice the methods of the present invention. Furthermore, different promoter-linked primers for transcription can also be used to practice the methods of the present invention. Moreover, different thermostable enzymes can be used to practice the methods of the present invention.

Gene Silencing Using mRNA-cDNA Hybrids: In Vitro Prostrate Cancer Model

As noted earlier, posttranscriptional gene silencing (PTGS) and RNA interference (RNAi) have been found capable of quelling specific gene activities in a variety of in vivo systems.

According to the invention provided herein, ectopic transfection of a sequence-specific messenger RNA (mRNA)-complementary DNA (cDNA) hybrid (instead of a transgene or ds-RNA) is used to induce intracellular gene silencing in human cells. Although previous transgene/ds-RNA transfection experiments showed that PTGS/RNAi effects are limited to plants and some simple animals, using the present invention, specific gene interference in higher eukaryotes, e.g. of bcl-2 expression in human LNCaP prostate cancer cells, using the D-RNAi has been successfully demonstrated.

Normal human prostatic secretory epithelial cells do not express bcl-2 protein, whereas neoplastic prostate tissues from androgen-ablation patients show an elevated level of this apoptosis-suppressing oncoprotein. It is known in the art that over-expression of bcl-2 protects prostate cancer cells from apoptosis in vitro, and confers resistance to androgen depletion in vivo. The tumorigenic and metastatic potentials of LNCaP cells are also significantly increased after bcl-2 stimulation by either androgen or transgene treatment. Such inhibition of apoptosis can be blocked by treatment with bcl-2 antisense oligonucleotides, but many apoptotic stimuli such as etoposide or phorbol ester cannot be blocked.

Figure 2:
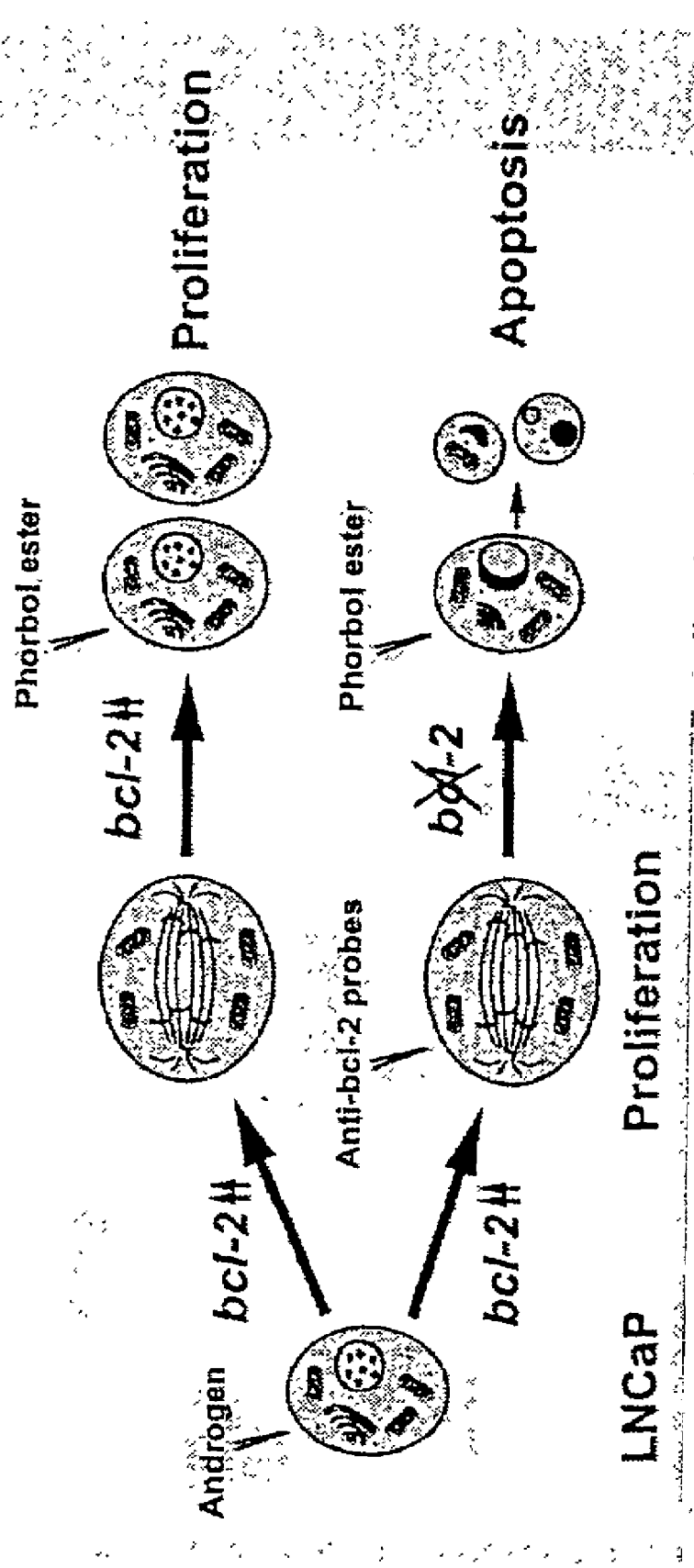
FIG. 2 shows a schematic representation of experimental procedures for testing interference of bcl-2 gene expression in androgen-treated human prostate cancer LNCaP cells, according to one embodiment of the present invention.

The potential utility of D-RNAi in preventing bcl-2 expression was therefore tested on androgen-stimulated LNCaP cells, expecting to increase cancer cell susceptibility to apoptotic stimuli and reduce tumorigenic outgrowth in vitro. Following previous findings, LNCaP cells were treated with dihydrotestersterone (100 nM 5α-anrostan-17β-ol-3-one) to block the apoptotic effect of phorbol ester (10 nM phorbol-12-myristate-13-acetate). When treated with the methods and compositions of this invention LNCaP cells induced an anti-bcl-2 D-RNAi effect to resume the apoptosis of the androgen- and phorbol ester-treated cancer cells (FIG. 2).

The identification of D-RNAi in human prostate cancer LNCaP cells is a breakthrough in the development of evolutionary gene silencing effects in higher level animal systems. When using RNA-DNA hybrids larger than 500 bases, a significant long-term (>6 days) PTGS/RNAi-like gene silencing effects in the mRNA-cDNA transfected cells was detected after an average 36-hour incubation with only one transfection.

Figure 3:
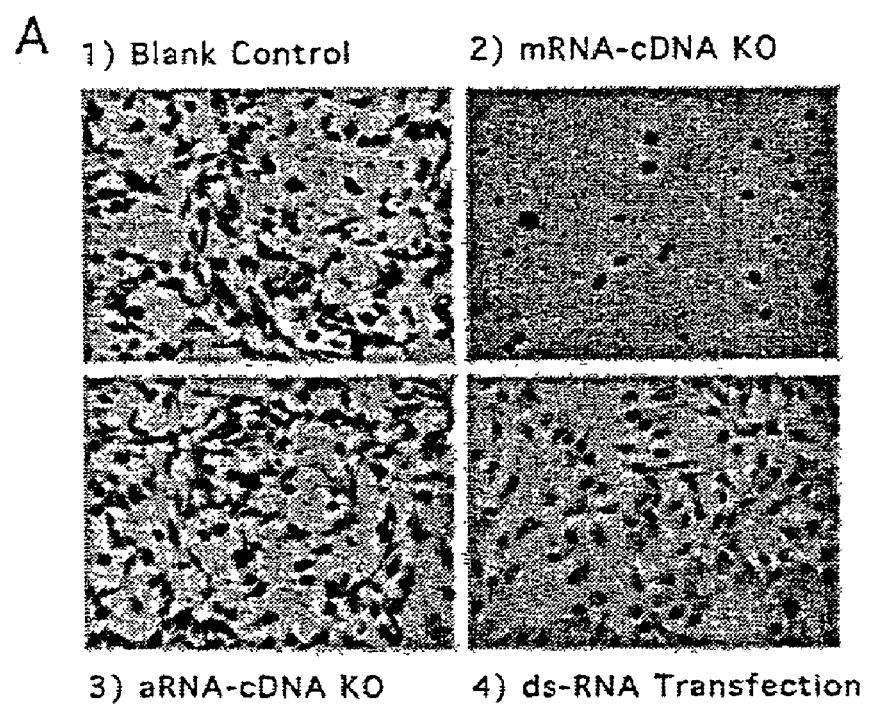
FIG. 3 shows different templates for bcl-2 gene interference, according to one embodiment of the present invention.
Figure 3:
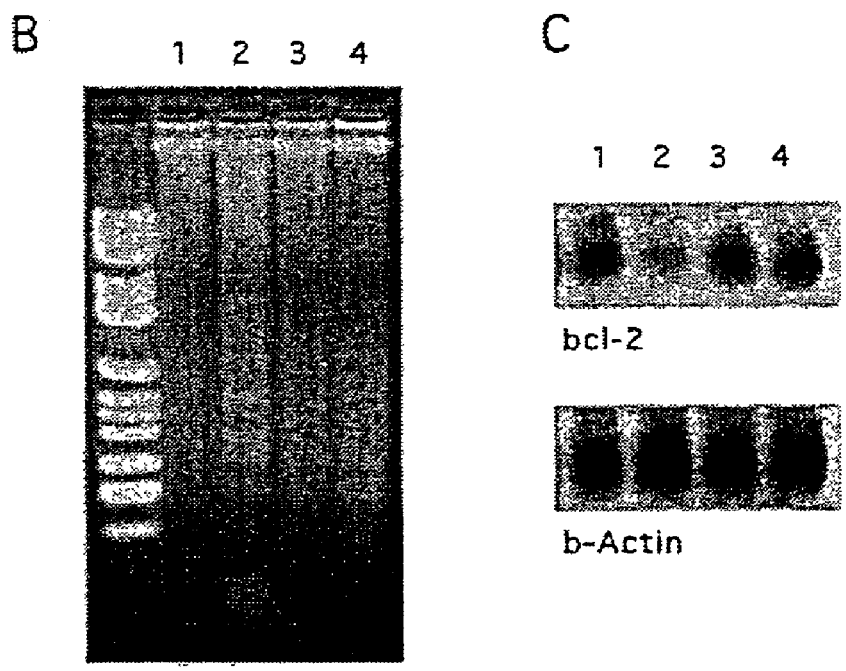

FIG. 3 shows the analysis of different templates for bcl-2 gene interference, namely: (1) blank control; (2) mRNA-cDNA hybrid; (3) aRNA-cDNA hybrid; and (4) ds-RNA in LNCaP cells. FIG. 3A shows changes of cell proliferation rate and morphology. Chromosomal DNAs were stained by propidium iodide. Although the ds-RNA transfection also showed minor morphological changes, a significant cell growth inhibition and chromosomal condensation only occurred in the mRNA-cDNA transfection (n=4). FIG. 3B shows genomic laddering patterns demonstrating apoptosis induction by the bcl-2 mRNA-cDNA transfection. FIG. 3C presents Northern blots showing a strong gene silencing effect of the mRNA-cDNA transfection in bcl-2 expression. As shown in FIG. 3, the transfection of bcl-2 mRNA-cDNA hybrids (5 nM) into LNCaP cells was sufficient to silence bcl-2 expression and cause apoptosis (chromosomal condensation and genomic DNA laddering fragmentation), which have not been found using double-stranded DNA (ds-RNA) or aRNA-cDNA hybrid transfections.

Each transfection of the antisense DNA probes provides a fast (within 24-hour incubation) and relatively short-term (2 to 3 days) gene knockout effect, which is in contrast to the relatively long-term initiation and maintenance effects of D-RNAi. Also, the concentration of mRNA-cDNA hybrids needed for enough biological effects is almost a half million fold less than that of antisense DNAs. This suggests that the effectiveness of D-RNAi is not the result of the cDNA part of a mRNA-cDNA hybrid. It is likely that an RdRp-like enzyme generates precursors of small RNAs or aRNAs based on an mRNA template, thereby maintaining the relatively long-term D-RNAi effects.

There are three major effects of PTGS, i.e., initiation, spreading and maintenance, all of which are also found in many inheritable RNAi phenomena. The initiation indicates that the onset of PTGS/RNAi takes a relatively long period of time (1~3 days) to develop enough small RNAs or short aRNAs for specific gene knockout. With the antisense transfection processes, it only takes several hours to reach the same gene silencing results but with much higher dosages and higher cytotoxicity. Also, unlike the short-term effectiveness of traditional antisense transfections, the PTGS/RNAi effects may spread from a transfected cell to neighboring cells and can be maintained for a very long time (weeks to lifetime) in a mother cell as well as its daughter cells.

Figure 4:
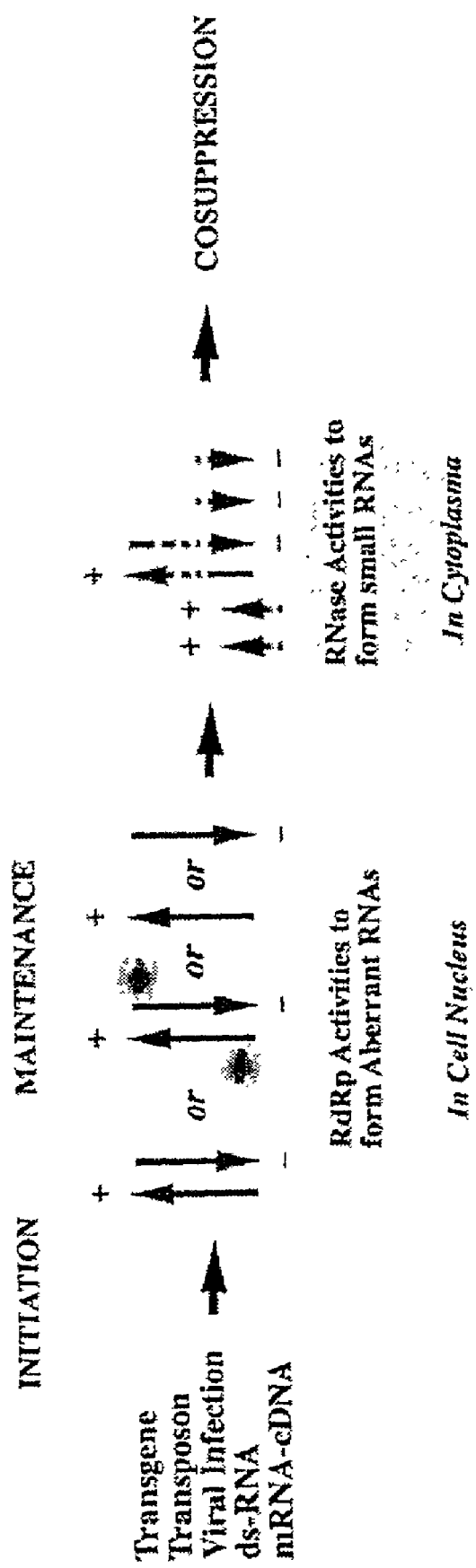
FIG. 4 shows a proposed model for long-term PTGS/RNAi/D-RNAi mechanisms.
Figure 5:
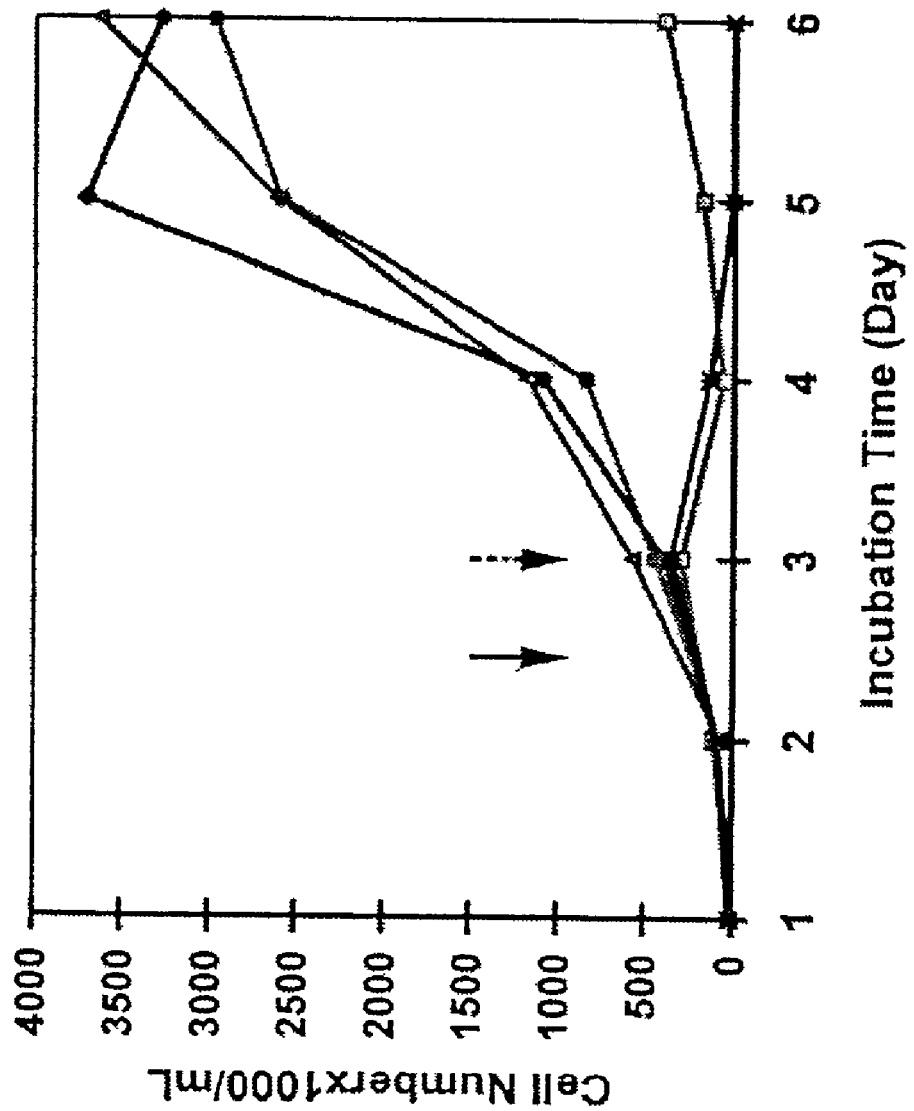
FIG. 5 shows a linear plot of the interaction between incubation time and cell growth number in the methods of the present invention.

The results of the experiments here suggest that D-RNAi shares some features of the PTGS/RNAi mechanisms. FIG. 4 shows a proposed model for long-term PTGS/RNAi/D-RNAi mechanisms. Initiation and maintenance periods are varied, depending on different living systems and transfected genes. Although the present invention is not limited to specific mechanisms, the potential RdRp-dependent mechanism of D-RNAi possesses the initiation and maintenance, but not spreading features of PTGS/RNAi effects. Because liposomal transfection methods offer only 30-40% transfection rate, a complete apoptosis induction in the LNCaP cell model used required at least two to three transfections (FIG. 5). FIG. 5 shows a linear plot of the interaction between incubation time (X) and cell growth number (Y), indicating no spreading effect of the D-RNAi. The black linear arrow shows the first addition of all tested probes, while the dotted arrow indicates the second addition of an mRNA-cDNA probe for double transfection analysis of D-RNAi. The proliferation rate of blank control (purple), aRNA-cDNA (blue) and ds-RNA (green) transfected cells were not affected, whereas the growth of mRNA-cDNA (red and black) transfected cells remarkably inhibited after 36-hour incubation (n=4). Because one transfection is not sufficient to reach the entire cell population, a more complete inhibition of cell growth is achieved after double transfections (black), indicating no spreading effect of D-RNAi.

Identification of a Potential RdRp-Like Enzyme for D-RNAi in LNCaP Cells

RNA polymerase II has been found to possess RNA-directed RNA synthesis activity (Filipovska et al., RNA 6: 41054 (2000); Modahl et al., *Mol. Cell Biol.* 20: 6030-6039 (2000)). Furthermore, the addition of low-dose α-amanitin (1.5 μg/ml), an RNA polymerase II-specific inhibitor derived from a mushroom *Amanita phalloides* toxin, abrogated the apoptosis induction of bcl-2 D-RNAi (FIG. 6).

Figure 6:
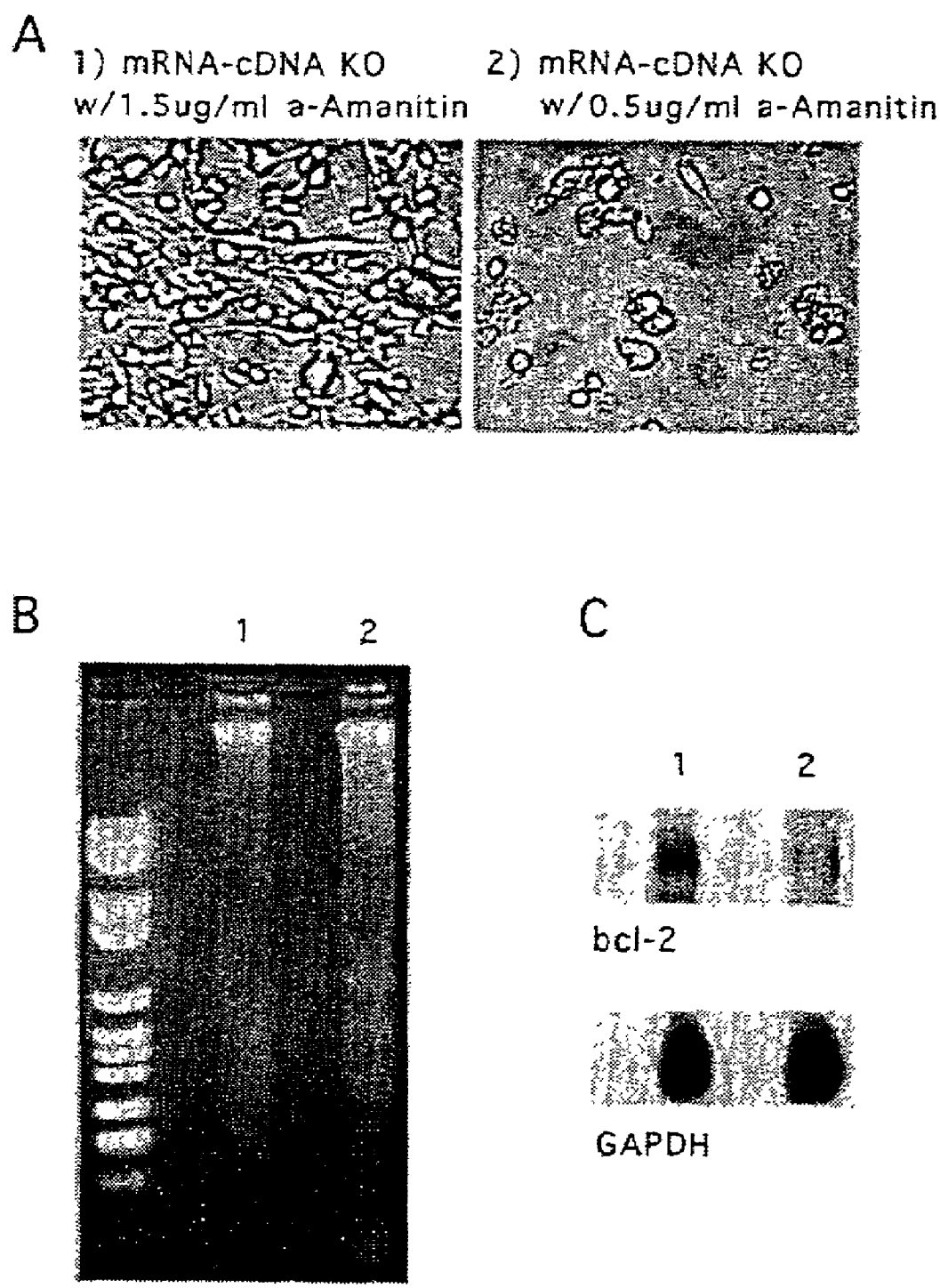
FIG. 6 shows potential D-RNAi-related RdRp enzymes by different α-amanitin sensitivity.

FIG. 6 shows an analysis of a potential D-RNAi-related RdRp enzyme by different α-amanitin sensitivity: (1) 1.5 μg/ml and (2) 0.5 μg/ml. FIG. 6A shows the changes of cell proliferation rate and morphology after addition of α-amanitin. A significant reduction of D-RNAi-induced apoptosis was detected in the 1.5 μg/ml α-amanitin addition (but not in the 0.5 μg/ml α-amanitin addition) after mRNA-cDNA transfection (n=3), showing a dose-dependent release of cell growth inhibition. FIG. 6B shows genomic laddering patterns demonstrating the blocking of the apoptotic induction effect of the bcl-2 mRNA-cDNA transfection by the 1.5 μg/ml α-amanitin addition. FIG. 6C shows Northern blots indicating that the bcl-2 silencing effect of D-RNAi was prevented.

It seems that the RNA polymerase II or another α-amanitin-sensitive RNA-directed polymerase is responsible for the RdRp activity of D-RNAi in human LNCaP cells. α-amanitin concentration up to 3.5 μg/ml can cause partial transcriptional inhibition without significant apoptosis induction in the dihydrotestersterone-treated LNCaP cells. Although the α-amanitin concentration tested suppressed only about half transcription activity, a remarkable inhibition of D-RNAi on bcl-2 has been detected, indicating that such potential RdRp enzyme is highly α-amanitin-sensitive. According to the replication of HDV, which is also an RNA-directed RNA synthesis procedure, the binding of RNA polymerase II to an RNA template requires an A-T rich domain but not necessarily a TATA-box as in the transcription of a DNA template.

Gene Silencing Using mRNA-cDNA Hybrids: In Vivo Model Targeting β-Catenin in a Developing Chicken Embryo The foregoing establishes that the novel mRNA-cDNA hybrids of the present invention can be used in a novel strategy to knock out targeted gene expression in vitro. As discussed below, the novel mRNA-cDNA strategy of the invention is also effective in knocking out gene expression in vivo.

As illustrated in the examples below, the methods and compositions of the invention are effective in knocking out targeted gene expression in vivo in a developing chicken embryo. For molecules, β-catenin was targeted because it has a critical role in development and oncogenesis, and for tissue, skin and liver were selected because the skin is accessible and the liver is an important organ. β-catenin is known to be involved in the regulation of growth control. It has been suggested that β-catenin is involved in neovasculogenesis and that it may work with VE-cadherin, which is not essential for the initial endothelial adhesion but is required in further vascular morphogenesis to properly form mature endothelial walls and blood vessels.

As discussed below, the experimental results establish that mRNA-cDNA hybrids are effective in inhibiting the expression of targeted genes, e.g., they potently inhibit β-catenin expression in the liver and skin of developing chick embryos. Thus, the results show that using an mRNA-cDNA duplex provides a powerful new strategy for gene silencing. A cDNA-aRNA duplex does not appear to work even though aRNA has been previously shown to suppress gene expression. This may be due to the low dosages used in the experiments here. However, this only underscores the fact that the mRNA-cDNA comprising compositions of the instant invention are effective even at low dosages. The results also show that this invention is effective in knocking out the targeted gene expression over a long period of time (>10 days). Further, it was observed that non-targeted organs appear to be normal, which implies that the compositions herein possess no overt toxicity. Thus, the invention offers the advantages of low dosage, stability, long term effectiveness, and lack of overt toxicity.

EXPERIMENTAL

The following examples serve to illustrate certain preferred embodiments and aspects of the present invention and are not to be construed as limiting the scope thereof.

In the experimental disclosure which follows, the following abbreviations apply: M (molar); mM (millimolar); μm (micromolar); mol (moles); pmol (picomolar); gm (grams); mg (milligrams); L (liters); ml (milliliters); μl (microliters); °C. (degrees Centigrade); cDNA (copy or complimentary DNA); DNA (deoxyribonucleic acid); ssDNA (single stranded DNA); dsDNA (double stranded DNA); dNTP (deoxyribonucleotide triphosphate); RNA (ribonucleic acid); PBS (phosphate buffered saline); NaCl (sodium chloride); HEPES (N-2-hydroxyethylpiperazine-N-2-ethanesulfonic acid); HBS (HEPES buffered saline); SDS (sodium dodecylsulfate); Tris-HCl (tris-hydroxymethylaminomethane-hydrochloride); and ATCC (American Type Culture Collection, Rockville, Md.).

All routine techniques and DNA manipulations, such as gel electrophoresis, were performed according to standard procedures. (See Sambrook et al., supra). All enzymes and buffer treatments were applied following the manufacture's recommendations (ROCHE BIOCHEMICALS, Indianapolis, Ind.). For Northern blots, mRNAs were fractionated on 1% formaldehyde-agarose gels and transferred onto nylon membranes (SCHLEICHER & SCHUELL, Keene, N H). Probes were labeled with the Prime-It II kit (STRATAGENE, La Jolla, Calif.) by random primer extension in the presence of [$^{32}$P]-dATP (>3000 Ci/mM, Amersham International, Arlington Heights, Ill.), and purified with Micro Bio-Spin chromatography columns (BIO-RAD, Hercules, Calif.). Hybridization was carried out in the mixture of 50% freshly deionized formamide (pH 7.0), 5×Denhardt's solution, 0.5% SDS, 4×SSPE and 250 μg/ml denatured salmon sperm DNAs (18 h, 42° C.). Membranes were sequentially washed twice in 2×SSC, 0.1% SDS (15 min, 25° C.), and once each in 0.2×

SSC, 0.1% SDS (15 min, 25° C.); and 0.2×SSC, 0.1% SDS (30 min, 65° C.) before autoradiography.

Example 1

Cell Fixation and Permeabilization

LNCaP cells, a prostate cancer cell line, were grown in RPMI 1640 medium supplemented with 2% fetal calf serum. A sample containing cells cultured in a 60 mm dish (70% full of cells) was trypsinized, collected and washed three times in 5 ml phosphate buffered saline (PBS, pH 7.2) at room temperature. After washing, the cells were suspended in 1 ml of ice-cold 10% formaldehyde solution in 0.15M NaCl. After one hour incubation on ice with occasional agitation, the cells were centrifuged at 13,000 rpm for 2 min, and washed three times in ice-cold PBS with vigorous pipetting. The collected cells were resuspended in 0.5% Nonidet P40 (NP40, B.D.H.) and incubated for one hour with frequent agitation. The cells were washed three times in ice-cold PBS containing 0.1M glycine, then resuspended in 1 ml of the same buffer with vigorous pipetting in order to be evenly separated into small aliquots and stored at —70° C. for up to a month.

Example 2

In-Cell Reverse Transcription and Poly-(N) Tailing of cDNAs

For reverse transcription of mRNAs in cells, twenty of the fixed cells were thawed, resuspended in 20 µl of ddH$_2$O, heated to 65° C. for 3 min and then cooled on ice. A 50 µl RT reaction was prepared, comprising 5 µl of 10× in-cell RT buffer (1.2M KCl, 0.5M Tris-HCl, 80 mM MgCl$_2$, 10 mM dithiothreitol, pH 8.1 at 42° C.), 5 µl of 5 mM dNTPs, 25 pmol oligo(dT)n-T7 promoter, 80 U RNase inhibitor and above cold cells. After reverse transcriptase (40 U) was added, the RT reaction was mixed and incubated at 55° C. for three hours. The cells were then washed once with PBS and resuspended in a 50 µl tailing reaction, comprising 2 mM dGTP, 10 µl of 5× tailing buffer (250 mM KCl, 50 mM Tris-HCl, 7.5 mM MgCl$_2$, pH 8.3 at 20° C.). The tailing reaction was heated at 94° C. for 3 min and then chilled in ice for mixing with terminal transferase (20 U), following further incubation at 37° C. for 20 min. Final reaction was stopped at 94° C. for 3 min. The reaction mixture was chilled in ice immediately, which formed the poly(N)-tailed cDNAs.

Example 3

Single-Cell mRNA Amplification

To increase the intracellular copies of whole mRNAs, the T7 promoter region of a poly(N)-tailed cDNA was served as a coding strand for the amplification by T7 RNA polymerase (Eberwine et al., *Proc. Natl. Acad. Sci. USA* 89: 3010-3014 (1992)). As few as one cell in 5 µl of above tailing reaction can be used to accomplish full-length aRNA amplification. An in-cell transcription reaction was prepared on ice, containing 25 pmol poly(dC)-20mer primer, 1 mM dNTPs, Pwo DNA polymerase (5 U), 5 µl of 10× Transcription buffer (Boehringer Mannheim), 2 mM NTPs and T7 RNA polymerase (2000 U). The hybridization of 20mer primer to the poly(N)-tailed cDNAs was incubated at 65° C. for 5 min to complete second strand cDNA synthesis and then RNA polymerase was added to start transcription. After four hour incubation at 37 ° C., the cDNA transcripts were isolated from both cells and supernatant, to be directly used in the following reverse transcription. The reaction was finally stopped at 94° C. for 3 min and chilled in ice.

Example 4

In Vitro Reverse Transcription and PCR Amplification

A 50 µl RT reaction was prepared, comprising 5 µl of 10×RT buffer (300 mM KCl, 0.5M Tris-HCl, 80 mM MgCl$_2$, 10 mM dithiothreitol, pH 8.3 at 20° C.), 5 µl of 5 mM dNTPs, 25 pmol oligo(dC)n-T7 promoter, 80 U Rnase inhibitor, ddH$_2$O and 5 µl of the above aRNA containing supernatant. After reverse transcriptase (40 U) was added, the RT reaction was vortexed and incubated at 55° C. for three hours. The resulting products of RT can be directly used in following PCR reaction (50 µl), comprising 5 µl of 10×PCR buffer (Boehringer Mannheim), 5 µl of 2 mM dNTPs, 25 pmol T7-20mer primer, 25 pmol poly(dT)-26mer primer, ddH$_2$O, 5 µl of above RT product and 3 U of Taq/Pwo long-extension DNA polymerase. The PCR reaction was subjected to thirty cycles of denaturation at 95° C. for 1 min, annealing at 55° C. for 1 min and extension at 72° C. for 3 min. The quality of final amplified cDNA library (20 µl) was assessed on a 1% formaldehyde-agarose gel, ranging from 100 bp to above 12 kb.

Example 5

RNA-PCR

Pre-cycling procedures. Primers used in RNA-PCR were as follows: a poly(dT)24 primer (5'-TTTTTTTTTTTTTTTTTTTTTTTT-3') (SEQ ID NO. 1) and an oligo(dC)$_{10}$N-promoter primer mixture comprising equal amounts of oligo(dC)$_{10}$G-T7 primer (5'-dCCAGTGAAT TGTAATACGACTCACTATAGGGAAC$_{10}$G-3') (SEQ ID NO. 2); oligo(dC)$_{10}$ A-T 7 primer (5'dCCAGTGAATTG-TAATACGACTCACTATAGGGAAC$_{10}$ A-3') (SEQ ID NO. 3); and oligo(dC)$_{10}$T-T7 primer (5'-dCCAGTGAATTG-TAATACGACTCACTATAGGGAAC$_{10}$ T-3') (SEQ ID NO. 4). The poly(dT)$_{24}$ primer was used to reverse transcribe mRNAs into first-strand cDNAs, while the oligo(dC)$_{10}$N-promoter primers functioned as a forward primer for second-strand cDNA extension from the poly(dG) end of the first-strand cDNAs and therefore RNA promoter incorporation. All oligonucleotides were synthetic and purified by high performance liquid chromatography (HPLC).

For in situ hybridization and cell preparations, fresh formaldehyde prefixed paraffin-embedded sections were dewaxed, dehydrated and refixed with 4% PFA, and then permeabilized with protemase K (10 µg/ml; Roche) after rinsing with 1×PBS. In situ hybridization was achieved with a denatured hybridization mixture within a 200 µl coverslip chamber, containing 40% formamide, 5×SSC, 1×Denhardt's reagent, 50 µg/ml salmon testis DNA, 100 µg/ml tRNA, 120 pmol/ml poly(dT)$_{24}$ primer, 10 pmol/ml biotin-labeled activin antisense probe (~700 bases in size) and tissue. After 10 h incubation at 65° C., sections were washed once with 5×SSC at 25° C. for 1 h and once with 0.5×SSC, 20% formamide at 60° C. for 30 min to remove unbound probes. A pre-heating step (68° C., 3 min) immersing the sections in a mild denaturing solution (25 mM Tris-HCl, pH 7.0, 1 mM EDTA, 20% formamide, 5% DMSO and 2 mM ascorbic acid) was performed to minimize secondary structures (including crosslinks) and to reduce the background. After the temperature was lowered to 45° C., 2,5-diaziridinyl-1,4-benzoquinone (200 µM; Sigma Chemical Co., St Louis, Mo.) was added to each incubation for a further 30 min. Finally, 0.1× SSC, 20% formamide was applied at 60° C. for 30 min to clean sections for chromogenic detection with straptavidin-alkaline phosphatase and Fast Red staining (Roche Biochemicals, Indianapolis, Ind.). Positive and negative results were observed and recorded under a microscope. RNase-free enzymes and DEPC-treated materials were required throughout the procedure.

Prostate cancer cells (20-150 cells) from in situ sections of patient tissues were isolated with a micromanipulator and directly used in RNA-PCR, while cultured LNCaP cells were preserved in 500 ld of ice-cold 10% formaldehyde in suspension buffer (0.15 M NaCl pH 7.0, 1 mM EDTA) for the following fixation and permeabilization procedure. After 1 h incubation with occasional agitation, fixed LNCaP cells were collected with microcon-50 filters (Amicon, Beverly, Mass.) and washed with 350 µl of ice-cold PBS with vigorous pipetting. The collection and wash were repeated at least once. The fixed cells were then permeabilized in 500 µl of 0.5% NP-40 for 1 h with frequent agitation. After that, three collections and washes were given to cells as before but using 350 µl of ice-cold PBS containing 0.1 M glycine instead. The cells were finally mixed with 0.1 µM poly(dT)$_{24}$ primer and resuspended in the same buffer with vigorous pipetting to evenly distribute them into small aliquots (~20 cells in 10 µl) for RNA-PCR. They could be stored at −80° C. for up to 2 weeks.

RNA-PCR. For amplification of intracellular mRNAs, more than 20 fixed cells were preheated at 94° C. for 5 min and applied to a reverse transcription (RT) reaction mixture (50 µl) on ice, comprising 10 µl of 5×RT&T buffer [100 mM Tris-HCl, pH 8.5 at 25° C., 600 mM KCl, 300 mM $(NH_4)_2SO_4$, 25 mM $MgCl_2$, 5 M betaine, 35 mM dithiothreitol, 10 mM spennidine and 25% dimethylsulphoxide (DMSO)], 1 µM poly(dT)$_{24}$ primer, dNTPs (1 mM each dATP, dGTP, dCTP and dTTP) and RNase inhibitors (10 U). After 6 U Caxboxydothernius hydrogenoformans (C. therm.) polymerase (Roche) was added, the reaction was incubated at 52° C. for 3 min and shifted to 65° C. for another 30 min. The first-strand cDNAs so obtained were collected with a Microcon-50 microconcentrater filter, washed once with 1×PBS and suspended in a tailing reaction (50 µl ), comprising 10 µl of 5×tailing buffer (250 mM KCl, 100 mM Tris-HCl, 4 mM $CoCl_2$, 10 mM $MgCl_2$, pH 8.3 at 20° C.) and 0.5 mM dGTP. After 75 U terminal transferase (Roche) was added, the reaction was incubated at 37° C. for 15 min, stopped by denaturation at 94° C. for 2 min and instantly mixed with 1 µM oligo(dC)$_{10}$N-promoter primer mixture. After briefly centrifuging, 3.5 U Taq DNA polymerase (Roche) and 1 mM of each of the dNTPs was added to form promoter-linked double-stranded cDNAs at 52° C. for 3 min, and then 72° C. for 7 min. The cells were broken by adding 1 vol of 2% Nonidet P-40 (NP-40; Sigma Chemical Co.) for 10 min, and then the double-stranded cDNAs were washed and recollected with a microcon-50 in autoclaved dd$H_2O$. This completed the pre-cycling steps for the following cycling amplification.

A transcription reaction (50 µl) was prepared, containing 10 µl of 5×RT&T buffer, rNTPs (1 mM each ATP, GTP, CTP and UTP), RNA inhibitors (10 U), T7 RNA polymerase (200 U; Roche) and the double-stranded cDNAs. After 2 h incubation at 37° C., the cDNA transcripts were isolated with a microcon-50 filter in 20 µl of DEPC-treated TE buffer (pH 7.0) and used directly for the next round of RNA-PCR without the tailing reaction, containing 10 µl of 5×RT&T buffer, 1 µM poly(dT)$_{24}$ primer, 1 µM oligo(dC)$_{10}$N-promoter primers, dNTPs (1 mM each), rNTPs (1 mM each), C. therm. polymerase, Taq DNA polymerase and the transcription products (20 pg). T7 RNA polymerase was renewed in every transcription step due to prior denaturation. The quality of mRNA products (20 µg) after three rounds of amplification was assessed on a 1% form aldehyde-agarose gel.

Northern blotting. mRNAs were fractionated on 1% formaldehyde-containing agarose gels and transferred to nylon membranes (Schleicher & Schuell, Keene, N. H.). Probes were labeled with the Pfime-It 11 kit (Stratagene, La Jolla, Calif.) by random primer extension in the presence of [$^{32}$P] dATP (>3000 Ci/mM; Amersham International, Arlington Heights, Ill.). Hybridization was carried out in the mixture of 50% freshly deionized formamide (pH 7.0), 5×Denhardt's solution, 0.5% SDS, 4×SSPE and 250 µg/ml denatured salmon sperm DNA (18 h, 42° C.). Membranes were washed twice in 2×SSC, 0.1% SDS (15 min, 25° C.), followed by once each in 0.2×SSC, 0.1% SDS (30 min., 65° C.) before autoradiography.

Example 6

Thermostable Cycling Amplification Procedure

Few fixed and permeabilized cells were applied to a reaction mixture (20 ml) on ice, comprising 2 ml of 10×RT&T buffer (400 mM Tris-HCl, pH 8.3 at 25° C., 400 mM NaCl, 80 mM $MgCl_2$, 5M betaine, 100 mM DTT and 20 mM spermidine), 1 mM Shh-antisense primer, 1 mM Shh-sense promoter-primer, 2 mM rNTPs, 2 mM dNTPs and RNase inhibitors (10 U). After C. therm./Taq DNA polymerase mixture (4 U) was added, the reaction was incubated at 52° C. for 3 min, at 65° C. for 30 min, at 94° C. for 3 min, at 52° C. for 3 min, and then at 68° C. for 3 min. A transcription reaction was prepared by adding T7 RNA polymerase (200 U) and C. therm. polymerase (6 U) mixture into above reaction. After one hour incubation at 37° C., the resulting mRNA transcripts were continuously reverse-transcribed into mRNA-cDNA hybrids at 52° C. for 3 min, and then at 65° C. for 30 min. The quality of amplified mRNA-cDNA products can be assessed on a 1% formaldehyde-agarose gel (Lin et al., Nucleic Acid Res. (1999)).

Example 7

Liposomal Transfection Procedure

Figure 8:
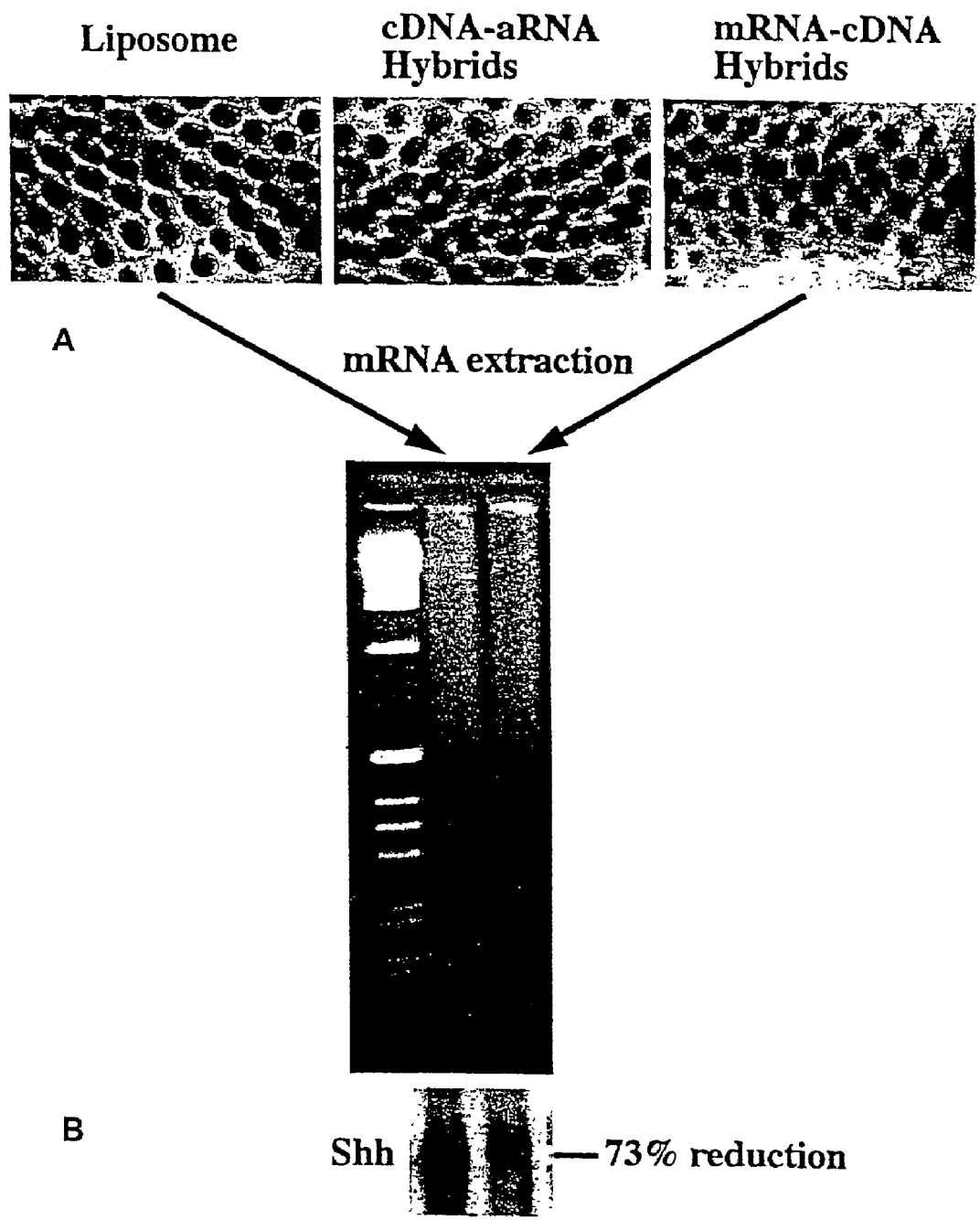
FIG. 8 shows Northern results of blank control and mRNA-cDNA hybrid in one embodiment of the present invention.

An mRNA-cDNA hybrid Shh probe (10 mg) was dissolved in 75 ml of Hepes buffer (pH 7.4). The resulting solution was mixed with 50 ml of DOTAP® liposome (1 mg/ml, Roche Biochemicals) on ice for 30 min., then subsequently applied to 60 mm diameter culture dishes containing four or five chicken skin explants. The skin explants were grown in HBSS medium. After a 36 hour incubation, the disturbance of feather growth was observed only in the mRNA-cDNA hybrid set while the blank-liposomal and cDNA-aRNA hybrid control have no effects (FIG. 8A). The Northern blot results of blank control and mRNA-cDNA hybrid set showed that a 73% gene silencing effect occurred by treating the mRNA-cDNA hybrid Shh probes (FIG. 8B).

Example 8

Gene Silencing Using a Chicken Embryo Model

This Example shows the effectiveness of an mRNA-cDNA strategy to knockout gene expression in vivo, using a developing chicken embryo as a model. In this example, β-catenin expression was targeted in the skin and liver of developing chick embryos. The mRNA-cDNA duplexes used for knocking β-catenin expression in vivo can be generated using the improved RNA-PCR technology discussed above.

For β-catenin, a double-stranded DNA template fragment, a pair of primers was designed based on the cDNA sequence. The central region for antisense targeting of β-catenin (aa 306-644) required four primers (i.e., primers A-D). The upstream (A) primer comprises the sequence 5'-ATGGCAATCAA-GAAAGTAAGC-3' (SEQ ID. NO. 5). The downstream (B) primer comprises the sequence 5'-GTACAACAACTGCA-CAAATAG-3' (SEQ ID. NO. 6). Another set of primers was required for the generation of the desired duplexes. The (C) primer was generated by adding the T7 promoter (RP) before the 5' end of the (A) primer. The (D) primer was generated by adding the T7 promoter before the 5' end of the (B) primer.

For mRNA-cDNA templates, B and C primers were used as primers in a polymerase chain reaction to generate promoter-linked double stranded cDNA. The promoter-linked double stranded cDNA was transcribed with T7 RNA polymerase for 2 h, and AMV reverse transcriptase for 1 hour Subsequently, the DRNAi hybrids were collected by filtration over a Microcon 50 (Amicon, Bedford, Mass.) column and eluted with 20 µl of elution buffer (20 mM HEPES). The final concentration of DRNAi is approximately 25 nM.

For the cDNA-aRNA template, A and D primers were used in a similar procedure as described above in the opposite orientation. The size of the hybrids was then determined on a 1% agarose gel. The hybrids were kept at −20° C. until use.

Fertilized eggs were obtained from SPAFAS farm (Preston, Conn.) and incubated in humidified incubator (Humidaire, New Madison, Ohio). At designated dates, eggs were put under a dissection microscope and the egg shells were sterilized. The shells were carefully cracked open and a window was made to get access to the embryos.

Figure 9:
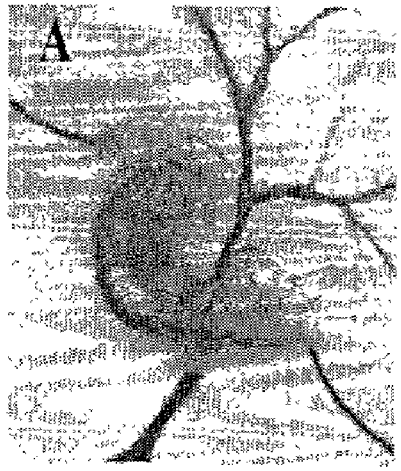
FIG. 9 shows the effect of in vivo delivery of mRNA-cDNA hybrid on targeted gene expression, in one embodiment of the present invention.
Figure 9:
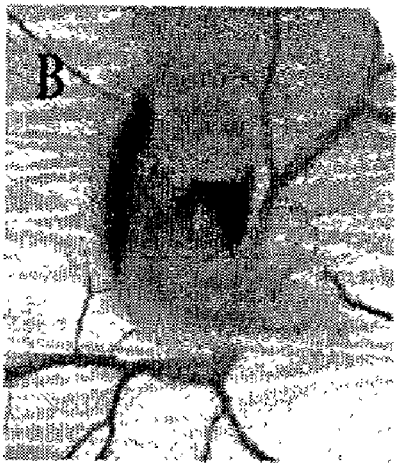
Figure 9:
Figure 9:
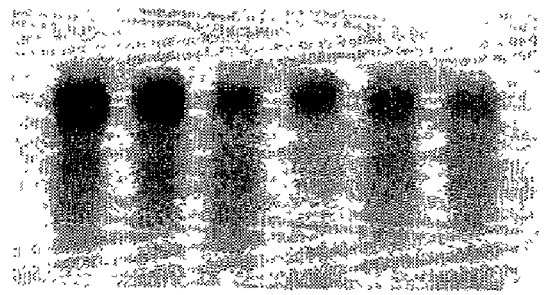

Using embryonic day three chicken embryos, either mRNA-cDNA or cDNA-aRNA (25 nM) was injected into the ventral body cavity, close to where the liver primordia would form. The mRNA-cDNA hybrid was mixed with DOTAP® liposome (Roche, Indianapolis, Ind.) at a ratio of 3:2. A 10% (v/v) fast green solution was added before the injection to increase visibility (FIG. 9B). The mixtures were injected into the ventral side near the liver primordia and below the heart using heat pulled capillary needles. After injection, the eggs were sealed with scotch tape and put back into a humidified incubator (Lyon Electric Company, Chula Vista, Calif.) at 39-40° C. until the harvesting time.

At designated days after injection, the embryos were removed, examined and photographed under a dissection microscope. While there are malformations, the embryos survived and there was no overt toxicity or overall perturbation of embryo development. The liver was closest to the injection site and is most dramatically affected in its phenotypes. Other regions, particularly the skin, are also affected by the diffused nucleotides.

Selected organs were removed and total RNAs were collected with an RNeasy kit (QIAGEN, Valencia, Calif.) for Northern analysis. RNAs were fractionated in an RNase free polyacrylamide gel (1%) and then transferred to Nylon membranes for 16-18 h. The tested gene was hybridized with a radiolabeled probe, and an autoradiograph was exposed. Northern blot hybridizations using RNA from dissected livers showed that β-catenin in the control livers remained expressed (lane 4-6, FIG. 9C), whereas the level of β-catenin mRNA was decreased dramatically (lane 1-3, FIG. 9D) after treatment with DRNAi directed against β-catenin. In this figure, C is hybridized to a β-catenin probe, while D is hybridized to a GAPDH probe, to show that equivalent concentrations were loaded. Controls used include liposome alone and similar concentrations of cDNA-aRNA.

Figure 10:
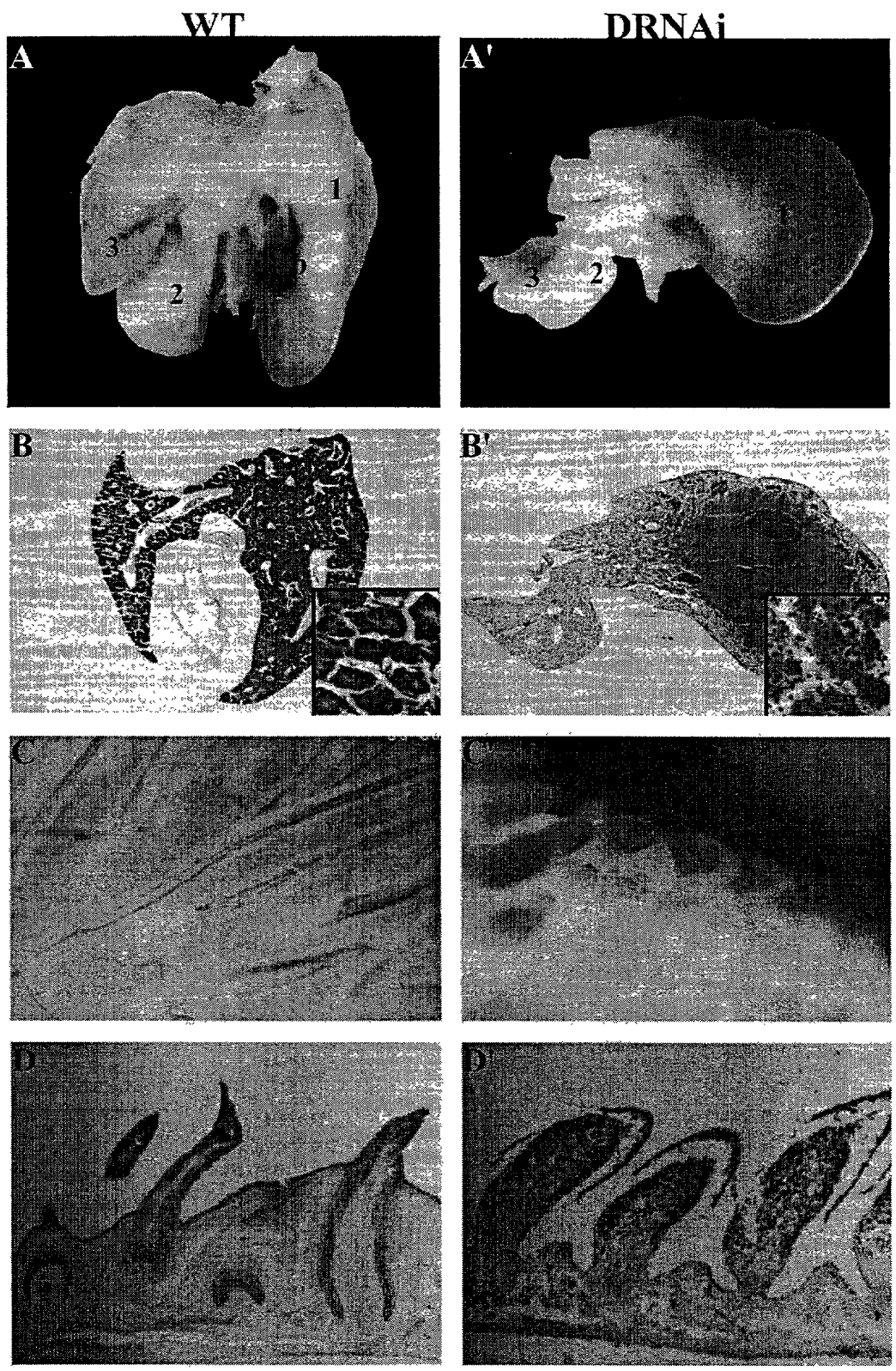
FIG. 10 illustrates the suppression of β-catenin, according to one embodiment of the present invention.

Livers after ten days of injection with mRNA-cDNA duplex showed an enlarged and engorged first lobe, but the size of the second and third lobes of the livers were dramatically decreased (FIG. 10A-A'). Histological sections of normal liver showed hepatic cords and sinusoidal space with few blood cells. In the β-catenin treated embryos, the general architecture of the hepatic cells in lobes 2 and 3 remained unchanged. However, in lobe 1 there are islands of abnormal regions. The endothelium development appears to be defective and blood is outside of the blood vessels. Abnormal types of hematopoietic cells are observed between the space of hepatocytes, particularly dominated by a population of small cells with round nuclei and scanty cytoplasm. In severely affected areas, hepatocytes were disrupted (FIG. 10B, B').

Since skin is exposed in the amniotic cavity and is most accessible to the nucleotides that leaked out, patches of skin that showed phenotypes were also observed. At embryonic day 13, skin should have formed elongated feather buds, with a primordial blood vessel running into its mesenchymal core. In the mRNA-cDNA β-catenin affected region, feather buds become engorged with blood, starting from the distal end of the feather tip (FIG. 10C, C'). The adjacent skin was normal (not shown), and works as a good control. Histological sections showed that the normal feather buds have continued their morphogenetic process with the epidermis invaginated to form the feather follicle walls, surrounding a mesenchymal core. In affected areas, the distal feather bud mesenchyme was full of engorged blood vessels and blood cells. Distal epidermis also detached from the feather mesenchyme, and proximal epidermis failed to invaginate to form follicles (FIG. 10D, D').

Example 9

Generation of bcl-2 RNA-DNA Hybrids

Four synthetic oligonucleotides were used in the generation of bcl-2 RNA-DNA hybrids as follows: T7-bcl2 primer (5'-dAAACGACGGCCAGTGAATTGTAATAC-GACTCACTATAGGCGGATGACTGAGTAC-CTGAACCGGC-3') (SEQ ID. NO. 7) and anti-bcl2 primer (5'-dCTTCTTCAGGCCAGGGAGGCATQG-3') (SEQ ID. NO. 8) for mRNA-cDNA hybrid (D-RNAi) probe preparation; T7-anti-bcl2 primer (5'-dAAACGACGGCCAGT-GAATTGTAATACGACTCACTATAGGCCT-TCTTCAGGCCAGGGAGGCATGG-3') (SEQ ID NO. 9) and bcl2 primer (5'-dGGATGACTGAGTACCTGAAC-CGGC-3') (SEQ ID NO. 10) for antisense RNA (aRNA)-cDNA hybrid (reverse D-RNAi) probe preparation. The design of the sequence-specific primers is based on the same principle used by PCR (50~60% G-C rich), while that of the promoter-linked primers however requires a higher G-C content (60~65%) working at the same annealing temperature as above sequence-specific primers due to their unmatched promoter regions. For example, new annealing temperature for the sequence-matched region of a promoter-linked primer is equal to [2° C.×(dA+dT)+3° C.×(dC+dG)]×5/6, not includ-

Example 10

Treatment of LNCaPCells to Induce bcl-2 Expression

LNCaP cells were obtained from the American Type Culture Collection (ATCC, Rockville, Md., and grown in RPMI 1640 medium supplemented with 10% fetal bovine serum with 100 μg/ml gentamycin at 37° C. under 10% $CO_2$. These cultured cells were treated with one dose of 100 nM 5α-anrostan-17β-ol-3-one to induce bcl-2 expression. For liposomal transfection of anti-bcl-2 probes, the probes (5 nM) in DOTAP liposome (Roche Biochemicals) were applied to a 60 mm culture dish which contained LNCaP cells at 15% confluency. After a 18-hour incubation, the cells took up about 60% of the probe-containing liposome. Uptake improved to 100% after 36 hours of incubation. The addition of α-amanitin was completed at the same time as the liposomal transfection. The apoptotic effect of phorbol-12-myristate -13-acetate (10 mM) was initiated at 12 hours after liposomal transfection. The mRNAs from the transfected LNCaP cells were isolated by poly-(dT) dextran columns (Qiagen, Santa Clarita, Calif.), fractionated on a 1% formaldehyde-agarose gel after a 36-hour incubation period, and transferred onto nylon membranes. After 48-hour transfection, genomic DNAs were isolated by an apoptotic DNA ladder kit (Roche Biochemicals) and assessed on a 2% agarose gel. Cell growth and morphology were examined by microscopy and cell counting, following known techniques. (See e.g., Lin et al., *Biochem. Biophys. Res. Commun.* 257: 187-192 (1999)).

Example 11

Probe Preparations from Androgen-Treated LNCaP Cells

For the generation of RNA-DNA hybrid probes, an RNA-polymerase cycling reaction (RNA-PCR) procedure was modified to generate either mRNA-cDNA or cDNA-aRNA hybrids. Total RNAs (0.2 μg) from androgen-treated LNCaP cells were applied to a reaction (50 μl in total) on ice, comprising 5 μl of 10×RT&T buffer (400 mM Tris-HCl, pH 8.3 at 25° C., 400 mM NaCl, 80 mM $MgCl_2$, 2 M betaine, 100 mM DTT and 20 mM spermidine), 1 μM sequence-specific primer for reverse transcription, 1 μM promoter-linked primer for cDNA-doublestranding, 2 mM rNTPs, 2 mM dNTPs and RNase inhibitors (10 U). After C. therm./Taq DNA polymerase mixture (4 U each) was added, the reaction was incubated at 52° C. for 3 min, 65° C. for 30 min, 94° C. for 3 min, 52° C. for 3 min and then 68° C. for 3 min. This formed a promoter-linked double-stranded cDNA for next step of transcriptional amplification up to 2000 fold/cycle. An in-vitro transcription reaction was performed by adding T7 RNA polymerase (160 U) and C. therm. polymerase (6 U) into above reaction. After one hour incubation at 37° C., the resulting mRNA transcripts were continuously reverse-transcribed into mRNA-cDNA hybrids at 52° C. for 3 min and then 65° C. for 30 min. The generation of cDNA-aRNA hybrids was the same procedure as aforementioned except using 1 μM sequence-specific primer for cDNA-doublestranding and 1 μM promoter-linked primer for reverse transcription. The RNA-PCR procedure can be reiterated to produce enough RNA-DNA hybrids for gene silencing analysis. For the preparation of double-stranded RNA probes, complementary RNA products were transcribed from both orientations of above promoter-linked double-stranded cDNAs and mixed together without reiterating reverse transcription activity. The quality of amplified probes were assessed on a 1% formaldehyde-agarose gel.

It is understood that the examples and embodiments described herein are for illustrative purposes only and that various modifications or changes in light thereof will be suggested to persons skilled in the art, and are to be included within the spirit and purview of the invention as set forth in the appended claims. All publications and patents cited herein are incorporated herein by reference in their entirety for all purposes.

We claim:

1. A method for inhibiting the expression of a target gene through a post-transcriptional gene silencing mechanism in a cell that expresses the targeted gene, comprising the steps of:
   a) providing a composition comprising an mRNA-cDNA hybrid duplex prior to contacting said cell, wherein the mRNA-cDNA hybrid duplex is capable of inhibiting the expression of said targeted gene in said cell, wherein said expression is inhibited through said post-transcriptional gene silencing mechanism, wherein said targeted gene is a β-cantenin gene, and wherein said cell is in the liver or skin of a chicken embryo; and
   b) contacting said cell with said composition under conditions such that the expression of said gene in said cell is inhibited,
   wherein the mRNA is a ribonucleic acid sequence in the sense orientation of said targeted gene and the cDNA is a deoxyribonucleic acid sequence in the anti-sense orientation of said targeted gene, and wherein the mRNA-cDNA hybrid duplex forms between said mRNA and said cDNA in a complementary region containing more than 500 base pairs.

2. The method of claim 1, wherein said mRNA-cDNA hybrid duplex inhibits the expression of said targeted gene, wherein said targeted gene comprises a β-catenin sequence encoding its amino acid domain from position 306 to 644.

3. The method of claim 1, wherein the composition consists of an mRNA-cDNA hybrid duplex capable of inhibiting the expression of said targeted gene, wherein the mRNA is a ribonucleic acid sequence in the sense orientation of said targeted gene and the cDNA is a deoxyribonucleic acid sequence in the anti-sense orientation of said targeted gene, wherein the mRNA-cDNA hybrid duplex forms between said mRNA and said cDNA in a complementary region containing more than 500 base pairs.

4. The method of claim 3, wherein said mRNA-cDNA hybrid duplex inhibits the expression of said targeted gene, wherein said targeted gene comprises a β-catenin sequence encoding its amino acid domain from position 306 to 644.

5. A method for inhibiting the expression of a target gene through a post-transcriptional gene silencing mechanism in a cell that expresses the targeted gene, comprising the steps of:
   a) providing a composition comprising an mRNA-cDNA hybrid duplex prior to contacting said cell, wherein the mRNA-cDNA hybrid duplex is capable of inhibiting the expression of said targeted gene in said cell, wherein said expression is inhibited through said post-transcriptional gene silencing mechanism, wherein said targeted gene is a β-cantenin gene, and wherein said cell is in the liver or skin of a chicken embryo; and
   b) contacting said cell with said composition under conditions such that the expression of said gene in said cell is inhibited,
   wherein the mRNA is a ribonucleic acid sequence in the sense orientation of said targeted gene and the cDNA is a deoxyribonucleic acid sequence in the anti-sense orientation of said targeted gene, and wherein the mRNA is a full-length transcript of said targeted gene larger than 500 base pairs.

6. The method of claim 5, wherein the mRNA is an unspliced mRNA transcript of the targeted gene.

7. The method of claim 5, wherein the mRNA is a spliced mRNA transcript of the targeted gene.

* * * * *

SEQUENCE LISTING

<160> NUMBER OF SEQ ID NOS: 10

<210> SEQ ID NO 1
<211> LENGTH: 24
<212> TYPE: DNA
<213> ORGANISM: Artificial
<220> FEATURE:
<223> OTHER INFORMATION: Primer

<400> SEQUENCE: 1 ttttttttttt tttttttttt tttt                24

<210> SEQ ID NO 2
<211> LENGTH: 44
<212> TYPE: DNA
<213> ORGANISM: Artificial
<220> FEATURE:
<223> OTHER INFORMATION: Primer

<400> SEQUENCE: 2

```
ccagtgaatt gtaatacgac tcactatagg gaaccccccc cccg           44

<210> SEQ ID NO 3
<211> LENGTH: 44
<212> TYPE: DNA
<213> ORGANISM: Artificial
<220> FEATURE:
<223> OTHER INFORMATION: Primer

<400> SEQUENCE: 3
ccagtgaatt gtaatacgac tcactatagg gaaccccccc ccca           44

<210> SEQ ID NO 4
<211> LENGTH: 44
<212> TYPE: DNA
<213> ORGANISM: Artificial
<220> FEATURE:
<223> OTHER INFORMATION: Primer

<400> SEQUENCE: 4
ccagtgaatt gtaatacgac tcactatagg gaaccccccc ccct           44

<210> SEQ ID NO 5
<211> LENGTH: 21
<212> TYPE: DNA
<213> ORGANISM: Artificial
<220> FEATURE:
<223> OTHER INFORMATION: Primer

<400> SEQUENCE: 5
atggcaatca agaaagtaag c                                    21

<210> SEQ ID NO 6
<211> LENGTH: 21
<212> TYPE: DNA
<213> ORGANISM: Artificial
<220> FEATURE:
<223> OTHER INFORMATION: Primer

<400> SEQUENCE: 6
gtacaacaac tgcacaaata g                                    21

<210> SEQ ID NO 7
<211> LENGTH: 64
<212> TYPE: DNA
<213> ORGANISM: Artificial
<220> FEATURE:
<223> OTHER INFORMATION: Primer

<400> SEQUENCE: 7
aaacgacggc cagtgaattg taatacgact cactataggc ggatgactga gtacctgaac   60
cggc                                                       64

<210> SEQ ID NO 8
<211> LENGTH: 24
<212> TYPE: DNA
<213> ORGANISM: Artificial
<220> FEATURE:
<223> OTHER INFORMATION: Primer

<400> SEQUENCE: 8
cttcttcagg ccagggaggc atgg                                 24

<210> SEQ ID NO 9
<211> LENGTH: 64
```

-continued

```
<212> TYPE: DNA
<213> ORGANISM: Artificial
<220> FEATURE:
<223> OTHER INFORMATION: Primer

<400> SEQUENCE: 9
aaacgacggc cagtgaattg taatacgact cactataggc cttcttcagg ccagggaggc      60
atgg                                                                  64

<210> SEQ ID NO 10
<211> LENGTH: 24
<212> TYPE: DNA
<213> ORGANISM: Artificial
<220> FEATURE:
<223> OTHER INFORMATION: Primer

<400> SEQUENCE: 10
ggatgactga gtacctgaac cggc                                            24
```